(12) United States Patent
Slate et al.

(10) Patent No.: US 10,792,426 B2
(45) Date of Patent: Oct. 6, 2020

(54) AUTOINJECTOR SYSTEM

(71) Applicant: AVANT MEDICAL CORP., Thousand Oaks, CA (US)

(72) Inventors: John B. Slate, Encinitas, CA (US); Michael W. Burk, San Marcos, CA (US); Richard J. Koerner, San Diego, CA (US); Corey M. Magers, Oceanside, CA (US); Andrew C. Barnes, San Diego, CA (US)

(73) Assignee: AVANT MEDICAL CORP., Thousand Oaks, CA (US)

( * ) Notice: Subject to any disclaimer, the term of this patent is extended or adjusted under 35 U.S.C. 154(b) by 132 days.

(21) Appl. No.: 15/952,296

(22) Filed: Apr. 13, 2018

(65) Prior Publication Data

US 2018/0228972 A1 Aug. 16, 2018

Related U.S. Application Data

(60) Division of application No. 12/993,163, filed as application No. PCT/US2009/044693 on May 20,
(Continued)

(51) Int. Cl.
*A61M 5/20* (2006.01)
*A61M 5/31* (2006.01)
(Continued)

(52) U.S. Cl.
CPC ............ *A61M 5/20* (2013.01); *A61M 5/3134* (2013.01); *A61M 5/3202* (2013.01);
(Continued)

(58) Field of Classification Search
CPC .............. A61M 5/3243; A61M 5/3257; A61M 2005/3258; A61M 5/326;
(Continued)

(56) References Cited

U.S. PATENT DOCUMENTS 2,525,398 A 10/1950 Collins
2,565,081 A 8/1951 Maynes
(Continued)

FOREIGN PATENT DOCUMENTS

AU 2009249027 11/2009
AU 2009249027 B2 8/2014
(Continued)

OTHER PUBLICATIONS

"Final Office Action" dated Oct. 18, 2016 issued related U.S. Appl. No. 13/269,150.
(Continued)

*Primary Examiner* — William R Carpenter
(74) *Attorney, Agent, or Firm* — Marshall, Gerstein & Borun LLP

(57) ABSTRACT

An autoinjector system for injecting a fluid medicament into a patient includes a re-usable autoinjector, and a disposable cassette loaded with a hypodermic syringe pre-filled with a fluid medicament. The autoinjector includes a first motor for injecting a needle of the hypodermic syringe into the patient and a second motor for expelling the fluid medicament from the syringe.

18 Claims, 15 Drawing Sheets

Related U.S. Application Data 2009, now Pat. No. 9,974,904, which is a continuation-in-part of application No. 12/178,447, filed on Jul. 23, 2008, now Pat. No. 8,052,645, and a continuation-in-part of application No. 12/123,888, filed on May 20, 2008, now Pat. No. 8,177,749.

(51) Int. Cl.
*A61M 5/32* (2006.01)
*A61M 5/315* (2006.01)

(52) U.S. Cl.
CPC ........... *A61M 5/3204* (2013.01); *A61M 5/326* (2013.01); *A61M 2005/206* (2013.01); *A61M 2005/208* (2013.01); *A61M 2005/2026* (2013.01); *A61M 2005/3142* (2013.01); *A61M 2005/31588* (2013.01); *A61M 2205/13* (2013.01); *A61M 2205/3365* (2013.01); *A61M 2205/50* (2013.01); *A61M 2205/581* (2013.01); *A61M 2205/583* (2013.01); *A61M 2205/6045* (2013.01)

(58) Field of Classification Search
CPC .. A61M 2005/3265; A61M 2005/3267; A61M 5/3271; A61M 5/3272
See application file for complete search history.

(56) References Cited

U.S. PATENT DOCUMENTS

| | | |
|---|---|---|
| 2,701,566 A | 2/1955 | Krug |
| 2,702,547 A | 2/1955 | Glass |
| 3,051,173 A | 8/1962 | Johnson et al. |
| 3,064,650 A | 11/1962 | Lewis |
| 3,203,269 A | 8/1965 | Perrine |
| 3,212,685 A | 10/1965 | Swan et al. |
| 3,623,474 A | 11/1971 | Heilman et al. |
| 3,720,211 A | 3/1973 | Kyrias |
| 3,859,996 A | 1/1975 | Mizzy et al. |
| 3,964,481 A | 6/1976 | Gourlandt et al. |
| 4,108,177 A | 8/1978 | Pistor |
| 4,231,368 A | 11/1980 | Becker |
| 4,273,122 A | 6/1981 | Whitney et al. |
| 4,276,879 A | 7/1981 | Yiournas |
| 4,373,526 A | 2/1983 | Kling |
| 4,421,107 A | 12/1983 | Estes et al. |
| 4,465,478 A | 8/1984 | Sabelman et al. |
| 4,493,704 A | 1/1985 | Beard et al. |
| 4,502,488 A | 3/1985 | Degironimo et al. |
| 4,504,263 A | 3/1985 | Steuer et al. |
| 4,515,590 A | 5/1985 | Daniel |
| 4,573,975 A | 3/1986 | Frist et al. |
| 4,585,439 A | 4/1986 | Michel |
| 4,613,328 A | 9/1986 | Boyd |
| 4,617,016 A | 10/1986 | Blomberg |
| 4,636,201 A | 1/1987 | Ambrose et al. |
| 4,685,903 A | 8/1987 | Cable et al. |
| 4,758,227 A | 7/1988 | Lancaster, Jr. et al. |
| 4,787,893 A | 11/1988 | Villette |
| 4,790,823 A | 12/1988 | Charton et al. |
| 4,838,857 A | 6/1989 | Strowe et al. |
| 4,877,034 A | 10/1989 | Atkins et al. |
| 4,902,279 A | 2/1990 | Schmidtz et al. |
| 4,919,596 A | 4/1990 | Slate et al. |
| 4,986,818 A | 1/1991 | Imbert et al. |
| 5,013,299 A | 5/1991 | Clark |
| 5,024,616 A * | 6/1991 | Ogle, II ............. A61M 5/3271 604/192 |
| 5,034,003 A | 7/1991 | Denance |
| 5,080,104 A | 1/1992 | Marks et al. |
| 5,085,641 A | 2/1992 | Sarnoff et al. |
| 5,092,843 A | 3/1992 | Monroe et al. |
| 5,098,400 A | 3/1992 | Crouse et al. |
| 5,112,317 A | 5/1992 | Michel |
| 5,114,404 A | 5/1992 | Paxton et al. |
| 5,114,406 A | 5/1992 | Gabriel et al. |
| 5,176,643 A | 1/1993 | Kramer et al. |
| 5,180,371 A | 1/1993 | Spinello |
| 5,200,604 A | 4/1993 | Rudko et al. |
| 5,221,268 A | 6/1993 | Barton et al. |
| 5,271,413 A | 12/1993 | Dalamagas et al. |
| 5,300,029 A | 4/1994 | Denance |
| 5,318,522 A | 6/1994 | D'Antonio |
| 5,352,196 A | 10/1994 | Haber et al. |
| 5,354,286 A | 10/1994 | Mesa et al. |
| 5,354,287 A | 10/1994 | Wacks |
| 5,382,785 A | 1/1995 | Rink |
| 5,393,497 A | 2/1995 | Haber et al. |
| 5,425,715 A | 6/1995 | Dalling et al. |
| 5,431,627 A | 7/1995 | Pastrone et al. |
| 5,451,210 A | 9/1995 | Kramer et al. |
| 5,456,670 A | 10/1995 | Neer et al. |
| 5,458,263 A | 10/1995 | Ciammitti et al. |
| 5,478,316 A | 12/1995 | Bitdinger et al. |
| 5,540,664 A | 7/1996 | Wyrick |
| 5,569,190 A | 10/1996 | D'Antonio |
| 5,569,197 A | 10/1996 | Helmus et al. |
| 5,569,212 A | 10/1996 | Brown |
| 5,578,014 A * | 11/1996 | Erez .................. A61F 7/10 604/192 |
| 5,584,815 A | 12/1996 | Pawelka et al. |
| 5,593,390 A | 1/1997 | Castellano et al. |
| 5,599,302 A | 2/1997 | Lilley et al. |
| 5,616,132 A | 4/1997 | Newman |
| 5,647,851 A | 7/1997 | Pokras |
| 5,647,853 A | 7/1997 | Feldmann et al. |
| 5,665,071 A | 9/1997 | Wyrick |
| 5,681,291 A | 10/1997 | Galli |
| 5,690,618 A | 11/1997 | Smith et al. |
| 5,695,472 A | 12/1997 | Wyrick |
| 5,698,189 A | 12/1997 | Rowe et al. |
| 5,709,662 A | 1/1998 | Olive et al. |
| 5,720,729 A | 2/1998 | Kriesel |
| 5,728,074 A | 3/1998 | Castellano et al. |
| 5,746,714 A | 5/1998 | Salo et al. |
| 5,779,683 A | 7/1998 | Meyer |
| 5,807,346 A | 9/1998 | Frezza |
| 5,843,036 A | 12/1998 | Olive et al. |
| 5,868,711 A | 2/1999 | Kramer et al. |
| 5,911,703 A | 6/1999 | Slate et al. |
| 5,919,159 A | 7/1999 | Lilley et al. |
| 5,921,963 A | 7/1999 | Erez et al. |
| 5,921,966 A | 7/1999 | Bendek et al. |
| 5,928,158 A | 7/1999 | Aristides |
| 5,945,046 A | 8/1999 | Hehl et al. |
| 5,957,897 A | 9/1999 | Jeffrey |
| 5,968,063 A | 10/1999 | Chu et al. |
| 5,993,423 A | 11/1999 | Choi |
| 6,019,745 A | 2/2000 | Gray |
| 6,019,747 A | 2/2000 | McPhee |
| 6,051,896 A | 4/2000 | Shibuya et al. |
| 6,090,082 A | 7/2000 | King et al. |
| 6,099,503 A | 8/2000 | Stradella |
| 6,104,941 A | 8/2000 | Huey et al. |
| 6,149,626 A | 11/2000 | Bachynsky et al. |
| 6,159,184 A | 12/2000 | Perez et al. |
| 6,171,276 B1 | 1/2001 | Lippe et al. |
| 6,171,283 B1 | 1/2001 | Perez et al. |
| 6,183,442 B1 | 2/2001 | Athanasiou et al. |
| 6,190,361 B1 * | 2/2001 | Gettig ................ A61M 5/3243 604/110 |
| 6,203,530 B1 | 3/2001 | Stewart, Sr. |
| 6,210,369 B1 | 4/2001 | Wilmot et al. |
| 6,213,987 B1 | 4/2001 | Hirsch et al. |
| 6,241,709 B1 | 6/2001 | Bechtold et al. |
| 6,245,043 B1 | 6/2001 | Villette |
| 6,248,093 B1 | 6/2001 | Moberg |
| 6,270,479 B1 | 8/2001 | Bergens et al. |
| 6,270,481 B1 | 8/2001 | Mason et al. |
| 6,280,421 B1 | 8/2001 | Kirchhofer et al. |
| 6,290,683 B1 | 9/2001 | Erez et al. |
| 6,344,030 B1 | 2/2002 | Duchon et al. |
| 6,344,032 B1 | 2/2002 | Perez et al. |

(56) References Cited

U.S. PATENT DOCUMENTS

| | | |
|---|---|---|
| 6,371,939 B2 | 4/2002 | Bergens et al. |
| 6,387,078 B1 | 5/2002 | Gillespie, III |
| 6,406,456 B1 | 6/2002 | Slate et al. |
| 6,447,482 B1 | 9/2002 | Ronborg et al. |
| 6,454,743 B1 | 9/2002 | Weber |
| 6,503,454 B1 | 1/2003 | Hadimioglu et al. |
| 6,520,928 B1 | 2/2003 | Junior |
| 6,540,672 B1 | 4/2003 | Simonsen et al. |
| 6,544,234 B1 | 4/2003 | Gabriel |
| 6,547,755 B1 | 4/2003 | Lippe et al. |
| 6,562,006 B1 | 5/2003 | Hjertman et al. |
| 6,569,123 B2 | 5/2003 | Alchas et al. |
| 6,569,127 B1 | 5/2003 | Fago et al. |
| 6,599,272 B1 | 7/2003 | Hjertman et al. |
| 6,641,561 B1 | 11/2003 | Hill et al. |
| 6,645,169 B1 | 11/2003 | Slate et al. |
| 6,645,177 B1 | 11/2003 | Shearn |
| 6,648,858 B2 | 11/2003 | Asbaghi |
| 6,652,483 B2 | 11/2003 | Slate et al. |
| D483,116 S | 12/2003 | Castellano |
| 6,656,163 B1 | 12/2003 | Marshall et al. |
| 6,656,164 B1 | 12/2003 | Smith |
| 6,669,664 B2 | 12/2003 | Slate et al. |
| 6,692,469 B1 | 2/2004 | Weekes et al. |
| 6,743,202 B2 | 6/2004 | Hirschman et al. |
| 6,746,427 B2 | 6/2004 | Duchon et al. |
| 6,752,787 B1 | 6/2004 | Causey, III et al. |
| 6,767,336 B1 | 7/2004 | Kaplan |
| 6,770,052 B2 | 8/2004 | Hill et al. |
| 6,796,957 B2 | 9/2004 | Carpenter et al. |
| 6,805,686 B1 | 10/2004 | Fathallah et al. |
| 6,808,507 B2 | 10/2004 | Roser |
| 6,817,986 B2 | 11/2004 | Slate et al. |
| 6,835,193 B2 | 12/2004 | Epstein et al. |
| 6,854,620 B2 | 2/2005 | Ramey |
| 6,890,319 B1 | 5/2005 | Crocker |
| 6,932,793 B1 | 8/2005 | Marshall et al. |
| 6,979,316 B1 | 12/2005 | Rubin et al. |
| 6,986,760 B2 | 1/2006 | Giambattista et al. |
| 7,008,399 B2 | 3/2006 | Larsen et al. |
| 7,011,649 B2 | 3/2006 | De La Serna et al. |
| 7,025,774 B2 | 4/2006 | Freeman et al. |
| 7,041,085 B2 | 5/2006 | Perez et al. |
| 7,066,909 B1 | 6/2006 | Peter et al. |
| 7,094,230 B2 | 8/2006 | Flaherty et al. |
| 7,104,400 B2 | 9/2006 | Kiehne |
| 7,118,553 B2 | 10/2006 | Scherer |
| 7,226,450 B2 | 6/2007 | Athanasiou et al. |
| 7,255,684 B2 | 8/2007 | Zubry |
| 7,273,469 B1 | 9/2007 | Chan et al. |
| 7,290,573 B2 | 11/2007 | Py et al. |
| 7,291,132 B2 | 11/2007 | DeRuntz et al. |
| 7,297,135 B2 | 11/2007 | Jeffrey |
| 7,297,136 B2 | 11/2007 | Wyrick |
| 7,357,790 B2 | 4/2008 | Hommann et al. |
| 7,361,160 B2 | 4/2008 | Hommann et al. |
| 7,370,759 B2 | 5/2008 | Hommann |
| 7,381,201 B2 | 6/2008 | Gilbert et al. |
| 7,390,319 B2 | 6/2008 | Friedman |
| 7,442,185 B2 | 10/2008 | Amark et al. |
| 7,449,012 B2 | 11/2008 | Young et al. |
| 7,476,217 B2 | 1/2009 | Martin et al. |
| 7,500,963 B2 | 3/2009 | Westbye et al. |
| 7,500,966 B2 | 3/2009 | Hommann |
| 7,553,294 B2 | 6/2009 | Lazzaro et al. |
| 7,597,685 B2 | 10/2009 | Olson |
| 7,635,348 B2 | 12/2009 | Raven et al. |
| 7,635,350 B2 | 12/2009 | Scherer |
| 7,648,483 B2 | 1/2010 | Edwards et al. |
| 7,654,987 B2 | 2/2010 | Hommann et al. |
| 7,670,314 B2 | 3/2010 | Wall et al. |
| 7,686,789 B2 | 3/2010 | Nemoto et al. |
| 7,731,686 B2 | 6/2010 | Edwards et al. |
| D619,706 S | 7/2010 | Schon et al. |
| 7,749,195 B2 | 7/2010 | Hommann |
| 7,760,099 B2 | 7/2010 | Knight |
| 7,785,292 B2 | 8/2010 | Harrison |
| D625,015 S | 10/2010 | Hansen et al. |
| 7,828,776 B2 | 11/2010 | Nemoto et al. |
| D628,690 S | 12/2010 | Galbraith |
| 7,857,791 B2 | 12/2010 | Jacobs et al. |
| 7,887,513 B2 | 2/2011 | Nemoto et al. |
| 7,901,377 B1 | 3/2011 | Harrison et al. |
| 7,909,796 B2 | 3/2011 | Weber |
| 7,918,823 B2 | 4/2011 | Edwards et al. |
| 7,922,695 B2 | 4/2011 | Wiegel et al. |
| D637,713 S | 5/2011 | Nord et al. |
| 7,938,803 B2 | 5/2011 | Mernoe et al. |
| D642,261 S | 7/2011 | York et al. |
| 7,976,499 B2 | 7/2011 | Grunhut et al. |
| 8,012,120 B2 | 9/2011 | Slate et al. |
| 8,012,125 B1 | 9/2011 | Fago et al. |
| 8,016,797 B2 | 9/2011 | Gratwohl et al. |
| 8,043,262 B2 | 10/2011 | Streit et al. |
| 8,048,037 B2 | 11/2011 | Kohlbrenner et al. |
| 8,052,645 B2 | 11/2011 | Slate et al. |
| D650,070 S | 12/2011 | Mori |
| 8,088,096 B2 | 1/2012 | Lauchard et al. |
| 8,105,271 B2 | 1/2012 | Matusch |
| 8,141,417 B2 | 3/2012 | Gibson et al. |
| 8,152,779 B2 | 4/2012 | Cabiri |
| 8,177,749 B2 | 5/2012 | Slate et al. |
| 8,221,356 B2 | 7/2012 | Enggaard et al. |
| 8,226,610 B2 | 7/2012 | Edwards et al. |
| 8,277,414 B2 | 10/2012 | Barrow-Williams et al. |
| 8,298,171 B2 | 10/2012 | Ishikawa et al. |
| 8,308,687 B2 | 11/2012 | Carrel et al. |
| 8,337,472 B2 | 12/2012 | Edginton et al. |
| D673,677 S | 1/2013 | Noda et al. |
| 8,343,103 B2 | 1/2013 | Moser |
| 8,376,985 B2 | 2/2013 | Pongpairochana et al. |
| D679,008 S | 3/2013 | Schroeder et al. |
| D679,391 S | 4/2013 | Chinowsky et al. |
| 8,491,538 B2 | 7/2013 | Kohlbrenner et al. |
| 8,523,803 B1 | 9/2013 | Favreau |
| 8,591,465 B2 | 11/2013 | Hommann |
| D694,879 S | 12/2013 | Julian et al. |
| 8,603,026 B2 | 12/2013 | Favreau |
| 8,603,027 B2 | 12/2013 | Favreau |
| 8,609,621 B2 | 12/2013 | Bedzyk et al. |
| 8,628,723 B2 | 1/2014 | Vandergaw |
| D702,343 S | 4/2014 | Dale et al. |
| D702,835 S | 4/2014 | Vinchon |
| 8,690,827 B2 | 4/2014 | Edwards et al. |
| 8,696,628 B2 | 4/2014 | Grunhut |
| 8,716,711 B2 | 5/2014 | Iwasaki |
| D718,439 S | 11/2014 | Woehr et al. |
| 8,900,204 B2 | 12/2014 | Geertsen |
| 8,911,410 B2 | 12/2014 | Ekman et al. |
| 8,960,827 B2 | 2/2015 | McMillin et al. |
| 8,961,473 B2 | 2/2015 | Heald |
| 8,968,255 B2 | 3/2015 | Oakland |
| 9,011,386 B2 | 4/2015 | Kronestedt et al. |
| 9,138,542 B2 | 9/2015 | Smith |
| D748,783 S | 2/2016 | Zhang et al. |
| 9,278,177 B2 | 3/2016 | Edwards et al. |
| D757,254 S | 5/2016 | Wohlfahrt et al. |
| D765,241 S | 8/2016 | Holland |
| D768,851 S | 10/2016 | Rozwadowski et al. |
| D768,852 S | 10/2016 | Rozwadowski et al. |
| 9,616,173 B2 | 4/2017 | Slate et al. |
| 9,649,443 B2 | 5/2017 | Klintenstedt et al. |
| 9,925,336 B2 | 3/2018 | Slate et al. |
| 9,974,904 B2 | 5/2018 | Burk et al. |
| 10,092,703 B2 | 10/2018 | Mounce et al. |
| 10,092,706 B2 | 10/2018 | Denzer et al. |
| 2001/0005781 A1 | 6/2001 | Bergens et al. |
| 2001/0011163 A1 | 8/2001 | Nolan et al. |
| 2001/0018937 A1 | 9/2001 | Nemoto |
| 2001/0034502 A1 | 10/2001 | Moberg et al. |
| 2001/0047153 A1 | 11/2001 | Trocki et al. |
| 2002/0016569 A1 | 2/2002 | Critchlow et al. |
| 2002/0022066 A1 | 2/2002 | Matsubayashi et al. |
| 2002/0029018 A1 | 3/2002 | Jeffrey |

(56) References Cited

U.S. PATENT DOCUMENTS

| | | |
|---|---|---|
| 2002/0095120 A1 | 7/2002 | Larsen et al. |
| 2002/0099334 A1 | 7/2002 | Hanson et al. |
| 2002/0133113 A1 | 9/2002 | Madsen et al. |
| 2002/0151855 A1 | 10/2002 | Douglas et al. |
| 2002/0156426 A1 | 10/2002 | Gagnieux et al. |
| 2003/0036725 A1 | 2/2003 | Lavi et al. |
| 2003/0050592 A1 | 3/2003 | Slate et al. |
| 2003/0065536 A1 | 4/2003 | Hansen et al. |
| 2003/0105430 A1 | 6/2003 | Lavi et al. |
| 2003/0233070 A1 | 12/2003 | De La Serna et al. |
| 2003/0236502 A1 | 12/2003 | De La Serna et al. |
| 2004/0019326 A1 | 1/2004 | Gilbert et al. |
| 2004/0039336 A1 | 2/2004 | Amark et al. |
| 2004/0054327 A1 | 3/2004 | Gillespie |
| 2004/0068266 A1 | 4/2004 | Delmotte |
| 2004/0116861 A1 | 6/2004 | Trocki et al. |
| 2004/0129803 A1 | 7/2004 | Dolder et al. |
| 2004/0133154 A1 | 7/2004 | Flaherty et al. |
| 2004/0133162 A1 | 7/2004 | Trocki et al. |
| 2004/0153008 A1 | 8/2004 | Sharf et al. |
| 2004/0225262 A1 | 11/2004 | Fathallah et al. |
| 2004/0258756 A1 | 12/2004 | McLoughlin |
| 2005/0020979 A1 | 1/2005 | Westbye et al. |
| 2005/0027255 A1 | 2/2005 | Lavi et al. |
| 2005/0033242 A1 | 2/2005 | Perez et al. |
| 2005/0049561 A1 | 3/2005 | Hommann et al. |
| 2005/0054987 A1 | 3/2005 | Perez et al. |
| 2005/0080377 A1 | 4/2005 | Sadowski et al. |
| 2005/0148869 A1 | 7/2005 | Masuda |
| 2005/0165404 A1 | 7/2005 | Miller |
| 2005/0171476 A1 | 8/2005 | Judson et al. |
| 2005/0171477 A1 | 8/2005 | Rubin et al. |
| 2005/0197650 A1 | 9/2005 | Sugimoto et al. |
| 2005/0203466 A1 | 9/2005 | Hommann et al. |
| 2005/0209569 A1 | 9/2005 | Ishikawa et al. |
| 2005/0261693 A1 | 11/2005 | Miller et al. |
| 2005/0277885 A1 | 12/2005 | Scherer |
| 2006/0022363 A1 | 2/2006 | Konno et al. |
| 2006/0030819 A1 | 2/2006 | Young et al. |
| 2006/0157064 A1 | 7/2006 | Davison et al. |
| 2006/0173408 A1 | 8/2006 | Wyrick |
| 2006/0251646 A1 | 11/2006 | Utku |
| 2006/0270985 A1 | 11/2006 | Hommann et al. |
| 2007/0021720 A1 | 1/2007 | Guillermo |
| 2007/0025879 A1 | 2/2007 | Vandergaw |
| 2007/0027430 A1 | 2/2007 | Hommann |
| 2007/0066938 A1 | 3/2007 | Iio et al. |
| 2007/0100281 A1 | 5/2007 | Morris et al. |
| 2007/0112301 A1 | 5/2007 | Preuthun et al. |
| 2007/0112310 A1 | 5/2007 | Lavi et al. |
| 2007/0118081 A1 | 5/2007 | Daily et al. |
| 2007/0135767 A1 | 6/2007 | Gillespie et al. |
| 2007/0142787 A1 | 6/2007 | Scherer |
| 2007/0149925 A1 | 6/2007 | Edwards et al. |
| 2007/0167920 A1 | 7/2007 | Hommann |
| 2007/0173770 A1 | 7/2007 | Stamp |
| 2007/0197954 A1 | 8/2007 | Keenan |
| 2007/0197968 A1 | 8/2007 | Pongpairochana et al. |
| 2007/0219498 A1 | 9/2007 | Malone et al. |
| 2007/0233001 A1 | 10/2007 | Burroughs et al. |
| 2007/0239114 A1 | 10/2007 | Edwards et al. |
| 2007/0250010 A1* | 10/2007 | Hohlfelder ............. A61C 19/08 604/154 |
| 2007/0265568 A1 | 11/2007 | Tsals et al. |
| 2008/0015510 A1 | 1/2008 | Sandoz et al. |
| 2008/0039795 A1 | 2/2008 | Slate et al. |
| 2008/0051711 A1 | 2/2008 | Mounce et al. |
| 2008/0051714 A1 | 2/2008 | Moberg et al. |
| 2008/0051715 A1 | 2/2008 | Young et al. |
| 2008/0097325 A1 | 4/2008 | Tanaka et al. |
| 2008/0132841 A1 | 6/2008 | Chiwanga et al. |
| 2008/0140007 A1 | 6/2008 | Glynn |
| 2008/0262423 A1 | 10/2008 | Ingram et al. |
| 2008/0262434 A1 | 10/2008 | Vaillancourt |
| 2008/0312602 A1 | 12/2008 | Barrow-Williams et al. |
| 2009/0018494 A1 | 1/2009 | Nemoto et al. |
| 2009/0018505 A1 | 1/2009 | Arguedas et al. |
| 2009/0024112 A1 | 1/2009 | Edwards et al. |
| 2009/0043253 A1 | 2/2009 | Podaima |
| 2009/0076383 A1 | 3/2009 | Toews et al. |
| 2009/0149744 A1 | 6/2009 | Nemoto et al. |
| 2009/0254060 A1 | 10/2009 | Hetherington |
| 2009/0270672 A1 | 10/2009 | Fago |
| 2009/0281505 A1 | 11/2009 | Hansen et al. |
| 2009/0292246 A1 | 11/2009 | Slate et al. |
| 2009/0299288 A1 | 12/2009 | Sie et al. |
| 2009/0299290 A1 | 12/2009 | Moberg |
| 2009/0312705 A1 | 12/2009 | Grunhut et al. |
| 2009/0322545 A1 | 12/2009 | Gibson et al. |
| 2009/0326459 A1 | 12/2009 | Shipway et al. |
| 2010/0016793 A1 | 1/2010 | Jennings et al. |
| 2010/0016795 A1 | 1/2010 | McLoughlin |
| 2010/0021456 A1 | 1/2010 | Miossec et al. |
| 2010/0022955 A1 | 1/2010 | Slate et al. |
| 2010/0036318 A1 | 2/2010 | Raday et al. |
| 2010/0042054 A1 | 2/2010 | Elahi et al. |
| 2010/0112679 A1 | 5/2010 | Vandergaw |
| 2010/0152655 A1 | 6/2010 | Stamp |
| 2010/0152659 A1 | 6/2010 | Streit et al. |
| 2010/0160894 A1 | 6/2010 | Julian et al. |
| 2010/0198060 A1 | 8/2010 | Fago et al. |
| 2010/0268170 A1 | 10/2010 | Carrel et al. |
| 2010/0312195 A1 | 12/2010 | Johansen et al. |
| 2011/0004165 A1 | 1/2011 | Iio et al. |
| 2011/0023281 A1 | 2/2011 | Schraga |
| 2011/0044998 A1 | 2/2011 | Bedian et al. |
| 2011/0047153 A1 | 2/2011 | Betz |
| 2011/0092915 A1 | 4/2011 | Olson et al. |
| 2011/0097229 A1 | 4/2011 | Cauley, III et al. |
| 2011/0098655 A1 | 4/2011 | Jennings et al. |
| 2011/0137286 A1 | 6/2011 | Mudd et al. |
| 2011/0144594 A1 | 6/2011 | Sund et al. |
| 2011/0152781 A1 | 6/2011 | Brunnberg et al. |
| 2011/0160580 A1 | 6/2011 | Perkins et al. |
| 2011/0166512 A1 | 7/2011 | Both et al. |
| 2011/0184383 A1 | 7/2011 | Hasegawa |
| 2011/0190693 A1 | 8/2011 | Takatsuka et al. |
| 2011/0190702 A1 | 8/2011 | Stumber |
| 2011/0196339 A1 | 8/2011 | Hirschel et al. |
| 2011/0202011 A1 | 8/2011 | Wozencroft |
| 2011/0213315 A1 | 9/2011 | Sweeney et al. |
| 2011/0224616 A1 | 9/2011 | Slate et al. |
| 2011/0224620 A1 | 9/2011 | Johansen et al. |
| 2011/0224621 A1 | 9/2011 | Johansen et al. |
| 2011/0230833 A1 | 9/2011 | Landman et al. |
| 2011/0245761 A1 | 10/2011 | Jennings et al. |
| 2011/0257596 A1 | 10/2011 | Gaudet |
| 2011/0257604 A1 | 10/2011 | Banik |
| 2011/0264046 A1 | 10/2011 | Nyholm et al. |
| 2011/0270220 A1 | 11/2011 | Genosar |
| 2012/0035472 A1 | 2/2012 | Bruce et al. |
| 2012/0035538 A1 | 2/2012 | Elmen et al. |
| 2012/0056019 A1 | 3/2012 | Renz et al. |
| 2012/0059319 A1 | 3/2012 | Segal |
| 2012/0089119 A1 | 4/2012 | Slate et al. |
| 2012/0101439 A9 | 4/2012 | Slate et al. |
| 2012/0172815 A1 | 7/2012 | Holmqvist |
| 2012/0238961 A1 | 9/2012 | Julian et al. |
| 2012/0253314 A1 | 10/2012 | Harish et al. |
| 2012/0265142 A1 | 10/2012 | Slate et al. |
| 2012/0296286 A1 | 11/2012 | Raab et al. |
| 2012/0323176 A1 | 12/2012 | Watanabe et al. |
| 2013/0018313 A1 | 1/2013 | Kramer et al. |
| 2013/0018315 A1 | 1/2013 | Blomquist |
| 2013/0030383 A1 | 1/2013 | Keitel |
| 2013/0035647 A1 | 2/2013 | Veasey et al. |
| 2013/0046248 A1 | 2/2013 | Raab |
| 2013/0110049 A1 | 5/2013 | Cronenberg et al. |
| 2013/0110054 A1 | 5/2013 | Raab et al. |
| 2013/0112521 A1 | 5/2013 | Ekman et al. |
| 2013/0131595 A1 | 5/2013 | Ekman et al. |
| 2013/0131601 A1 | 5/2013 | Pommereau et al. |
| 2013/0190719 A1 | 7/2013 | Smith et al. |
| 2013/0190721 A1 | 7/2013 | Kemp et al. |

(56) References Cited

U.S. PATENT DOCUMENTS

| | | |
|---|---|---|
| 2013/0204198 A1 | 8/2013 | Burnell et al. |
| 2013/0204204 A1 | 8/2013 | Butler et al. |
| 2013/0218092 A1 | 8/2013 | Davies et al. |
| 2013/0226091 A1 | 8/2013 | Nzike et al. |
| 2013/0261558 A1 | 10/2013 | Hourmand et al. |
| 2013/0274668 A1 | 10/2013 | Barrow-Williams et al. |
| 2013/0289491 A1 | 10/2013 | Kramer et al. |
| 2013/0310744 A1 | 11/2013 | Brereton et al. |
| 2013/0310761 A1 | 11/2013 | Plumptre |
| 2013/0317430 A1 | 11/2013 | Brereton et al. |
| 2013/0317480 A1 | 11/2013 | Reber et al. |
| 2013/0324935 A1 | 12/2013 | Brereton et al. |
| 2013/0338601 A1 | 12/2013 | Cowe |
| 2014/0046259 A1 | 2/2014 | Reber et al. |
| 2014/0148784 A1 | 5/2014 | Anderson et al. |
| 2014/0194854 A1 | 7/2014 | Tsals |
| 2014/0236087 A1 | 8/2014 | Alderete, Jr. et al. |
| 2014/0257197 A1 | 9/2014 | Madsen et al. |
| 2014/0276448 A1 | 9/2014 | Muller-Pathle et al. |
| 2014/0296825 A1 | 10/2014 | Lemaire et al. |
| 2014/0303556 A1 | 10/2014 | Travanty |
| 2014/0316369 A1 | 10/2014 | Centeno et al. |
| 2014/0330203 A1 | 11/2014 | McLoughlin et al. |
| 2014/0330216 A1 | 11/2014 | Weaver et al. |
| 2014/0336590 A1 | 11/2014 | Hourmand et al. |
| 2014/0364808 A1 | 12/2014 | Niklaus et al. |
| 2015/0045729 A1 | 2/2015 | Denzer et al. |
| 2015/0080809 A1 | 3/2015 | Dasbach et al. |
| 2015/0136809 A1 | 5/2015 | Hamann et al. |
| 2015/0141923 A1 | 5/2015 | Wurmbauer et al. |
| 2015/0151046 A1 | 6/2015 | Nagel et al. |
| 2015/0165130 A1 | 6/2015 | Butler et al. |
| 2015/0217057 A1 | 8/2015 | Hogdahl |
| 2016/0022914 A1 | 1/2016 | Mounce et al. |
| 2016/0120751 A1 | 5/2016 | Mounce et al. |
| 2016/0271326 A1 | 9/2016 | Slate et al. |
| 2017/0043105 A1 | 2/2017 | Elmen |
| 2017/0157326 A1 | 6/2017 | Slate et al. |

FOREIGN PATENT DOCUMENTS

| | | |
|---|---|---|
| CA | 2074565 A1 | 1/1993 |
| CA | 2074565 | 2/2000 |
| CA | 2594627 A1 | 8/2006 |
| DE | 102007061775 | 7/2009 |
| DE | 102007061775 A1 | 7/2009 |
| EP | 1219312 A2 | 7/2002 |
| EP | 1227423 | 7/2002 |
| EP | 1227423 A1 | 7/2002 |
| EP | 1518575 A1 | 3/2005 |
| EP | 0620748 B1 | 7/2010 |
| ES | 2121536 | 11/1998 |
| ES | 2121536 A1 | 11/1998 |
| FR | 2390175 | 12/1978 |
| FR | 2390175 A2 | 12/1978 |
| FR | 2581548 A1 | 11/1986 |
| FR | 2592307 | 7/1987 |
| FR | 2592307 A1 | 7/1987 |
| FR | 2622457 | 5/1989 |
| FR | 2622457 A1 | 5/1989 |
| FR | 2581548 | 7/1990 |
| FR | 2716375 | 8/1995 |
| FR | 2716375 A1 | 8/1995 |
| IL | 87559 A | 6/1993 |
| IL | 877559 | 6/1993 |
| IL | 87599 | 8/1993 |
| JP | S63139563 | 6/1988 |
| JP | S63139563 A | 6/1988 |
| JP | 2008157 | 1/1990 |
| JP | H07503384 | 4/1995 |
| JP | H07503384 A | 4/1995 |
| JP | H07185000 | 7/1995 |
| JP | H07185000 A | 7/1995 |
| JP | H11-276583 A | 10/1999 |
| JP | 2000-237309 A | 9/2000 |
| JP | 2001518366 | 10/2001 |
| JP | 2001518366 A | 10/2001 |
| JP | 20020531228 A | 9/2002 |
| JP | 2002543931 | 12/2002 |
| JP | 2002543931 A | 12/2002 |
| JP | 2003220142 | 8/2003 |
| JP | 2003220142 A | 8/2003 |
| JP | 20020531228 | 8/2004 |
| JP | 2005-131007 A | 5/2005 |
| JP | 205514082 | 5/2005 |
| JP | 2005514082 A | 5/2005 |
| JP | 2005-287676 A | 10/2005 |
| JP | 2006507061 | 3/2006 |
| JP | 2006507061 A | 3/2006 |
| JP | 2007500561 | 3/2006 |
| JP | 2006-523507 A | 10/2006 |
| JP | 2006528040 | 12/2006 |
| JP | 2006528040 A | 12/2006 |
| JP | 2007500561 A | 1/2007 |
| JP | 2007-507260 A | 3/2007 |
| JP | 2007111518 | 5/2007 |
| JP | 2007111518 A | 5/2007 |
| JP | 2007529243 | 10/2007 |
| JP | 2007529243 A | 10/2007 |
| JP | 2008508961 | 3/2008 |
| JP | 2008508961 A | 3/2008 |
| JP | 2010-051828 A | 3/2010 |
| JP | 2010511414 A | 4/2010 |
| JP | 20100511414 | 4/2010 |
| JP | 2015186876 | 10/2015 |
| JP | 2015186876 A | 10/2015 |
| JP | 2017-023813 A | 2/2017 |
| TW | 200833383 A | 8/2008 |
| TW | 200833387 A | 8/2008 |
| TW | 200836787 A | 9/2008 |
| TW | 200840606 A | 10/2008 |
| TW | 201004667 A | 2/2010 |
| TW | 201004668 A | 2/2010 |
| WO | 1986006967 | 10/1986 |
| WO | WO-1986006967 A1 | 12/1986 |
| WO | 1987003494 | 6/1987 |
| WO | WO-1987003494 A1 | 6/1987 |
| WO | 1987007160 | 12/1987 |
| WO | WO-1987007160 A1 | 12/1987 |
| WO | 01/089634 | 12/1991 |
| WO | 1991018634 | 12/1991 |
| WO | WO-1991018634 A1 | 12/1991 |
| WO | 1992006725 | 4/1992 |
| WO | WO-1992006725 A1 | 4/1992 |
| WO | 1992008506 | 5/1992 |
| WO | WO-1992008506 A1 | 5/1992 |
| WO | 1992021392 | 12/1992 |
| WO | WO-1992021392 A1 | 12/1992 |
| WO | 1993002728 | 2/1993 |
| WO | WO-1993002728 A1 | 2/1993 |
| WO | 1993013817 | 7/1993 |
| WO | WO-1993013817 A1 | 7/1993 |
| WO | 1993024160 | 12/1993 |
| WO | 1993025256 | 12/1993 |
| WO | WO-1993024160 A1 | 12/1993 |
| WO | WO-1993025256 A1 | 12/1993 |
| WO | 1994006494 | 3/1994 |
| WO | WO-1994006494 A1 | 3/1994 |
| WO | WO-94/07553 A1 | 4/1994 |
| WO | 1995021645 | 8/1995 |
| WO | WO-1995021645 A1 | 8/1995 |
| WO | 1995025555 | 9/1995 |
| WO | WO-1995025555 A1 | 9/1995 |
| WO | 1995031235 | 11/1995 |
| WO | WO-1995031235 A1 | 11/1995 |
| WO | 1995034333 | 12/1995 |
| WO | WO-1995034333 A2 | 12/1995 |
| WO | 1996000594 | 1/1996 |
| WO | WO-1996000594 A1 | 1/1996 |
| WO | 1996021482 | 7/1996 |
| WO | WO-1996021482 A2 | 7/1996 |
| WO | 1996026754 | 9/1996 |
| WO | WO-1996026754 A2 | 9/1996 |
| WO | 1996038190 | 12/1996 |

(56) References Cited

FOREIGN PATENT DOCUMENTS

| | | |
|---|---|---|
| WO | WO-1996038190 A1 | 12/1996 |
| WO | 1997007839 | 3/1997 |
| WO | WO-1997007839 A1 | 3/1997 |
| WO | 1997031665 | 9/1997 |
| WO | WO-1997031665 A1 | 9/1997 |
| WO | 1998013077 | 4/1998 |
| WO | 1998017332 | 4/1998 |
| WO | WO-1998013077 A2 | 4/1998 |
| WO | WO-1998017332 A2 | 4/1998 |
| WO | 1998021408 | 5/1998 |
| WO | WO-1998021408 A1 | 5/1998 |
| WO | WO-98/28032 A1 | 7/1998 |
| WO | 99/17823 | 4/1999 |
| WO | 1999017823 | 4/1999 |
| WO | 1999020327 | 4/1999 |
| WO | WO-99/17823 A1 | 4/1999 |
| WO | WO-1999017823 A1 | 4/1999 |
| WO | WO-1999020327 A2 | 4/1999 |
| WO | 1999021600 | 5/1999 |
| WO | WO-1999021600 A2 | 5/1999 |
| WO | 99/65548 | 12/1999 |
| WO | WO-99/65548 A1 | 12/1999 |
| WO | 2000002605 | 1/2000 |
| WO | WO-2000002605 | 1/2000 |
| WO | 2000009186 | 2/2000 |
| WO | WO-2000009186 A2 | 2/2000 |
| WO | 2000024441 | 5/2000 |
| WO | 2000025846 | 5/2000 |
| WO | WO-2000024441 | 5/2000 |
| WO | WO-2000025846 | 5/2000 |
| WO | 2001000261 | 1/2001 |
| WO | WO-2001000261 | 1/2001 |
| WO | 2001037903 | 5/2001 |
| WO | WO-2001037903 | 5/2001 |
| WO | 01/41835 | 6/2001 |
| WO | 2001041835 | 6/2001 |
| WO | WO-01/41835 A2 | 6/2001 |
| WO | WO-2001041835 | 6/2001 |
| WO | 2001089634 | 11/2001 |
| WO | WO-01/089634 A2 | 11/2001 |
| WO | WO-2001089634 | 11/2001 |
| WO | 02/07812 | 1/2002 |
| WO | 2002007812 | 1/2002 |
| WO | WO-02/07812 A2 | 1/2002 |
| WO | WO-2002007812 | 1/2002 |
| WO | 2002/11792 | 2/2002 |
| WO | WO-2002/11792 A1 | 2/2002 |
| WO | 02/49691 | 6/2002 |
| WO | 2002049691 | 6/2002 |
| WO | WO-02/49691 A2 | 6/2002 |
| WO | WO-2002049691 | 6/2002 |
| WO | 2002/060513 | 8/2002 |
| WO | WO-2002/060513 A2 | 8/2002 |
| WO | 02/092153 | 11/2002 |
| WO | 2002092153 | 11/2002 |
| WO | WO-02/092153 A2 | 11/2002 |
| WO | WO-2002092153 | 11/2002 |
| WO | 03/03934 A1 | 1/2003 |
| WO | 03/006099 | 1/2003 |
| WO | 03/008023 | 1/2003 |
| WO | 2003006099 | 1/2003 |
| WO | 2003008023 | 1/2003 |
| WO | WO-03/006099 A1 | 1/2003 |
| WO | WO-03/008023 A1 | 1/2003 |
| WO | WO-2003006099 | 1/2003 |
| WO | WO-2003008023 | 1/2003 |
| WO | 2003/024385 | 3/2003 |
| WO | WO-2003/024385 A1 | 3/2003 |
| WO | 03/039634 | 5/2003 |
| WO | WO-03/039634 A1 | 5/2003 |
| WO | 03/047663 | 6/2003 |
| WO | 2003/047659 | 6/2003 |
| WO | 2003047663 | 6/2003 |
| WO | WO-03/047663 A1 | 6/2003 |
| WO | WO-2003/047659 A1 | 6/2003 |
| WO | WO-2003047663 | 6/2003 |
| WO | 03/90509 | 11/2003 |
| WO | 2003090509 | 11/2003 |
| WO | WO-03/90509 A2 | 11/2003 |
| WO | WO-2003090509 | 11/2003 |
| WO | 03/103749 | 12/2003 |
| WO | 2003103749 | 12/2003 |
| WO | WO-03/103749 A2 | 12/2003 |
| WO | WO-2003103749 | 12/2003 |
| WO | 2004/004809 | 1/2004 |
| WO | WO-2004/004809 A1 | 1/2004 |
| WO | WO-2004/004825 A2 | 1/2004 |
| WO | 2004/069303 | 8/2004 |
| WO | WO-2004/069303 A2 | 8/2004 |
| WO | 2004/084795 A1 | 10/2004 |
| WO | 2004/108193 | 12/2004 |
| WO | WO-2004/108193 A1 | 12/2004 |
| WO | WO-2005/032449 A1 | 4/2005 |
| WO | 2005/053771 | 6/2005 |
| WO | WO-2005/053771 A2 | 6/2005 |
| WO | 2005/070481 | 8/2005 |
| WO | WO-2005/070481 A1 | 8/2005 |
| WO | 2005/079440 | 9/2005 |
| WO | 2005089831 | 9/2005 |
| WO | WO-2005/079440 A2 | 9/2005 |
| WO | WO-2005089831 A1 | 9/2005 |
| WO | 2005/094923 | 10/2005 |
| WO | WO-2005/094923 A1 | 10/2005 |
| WO | 2006015501 | 2/2006 |
| WO | 2006017732 | 2/2006 |
| WO | 2006020609 | 2/2006 |
| WO | WO-2006015501 A1 | 2/2006 |
| WO | WO-2006017732 A2 | 2/2006 |
| WO | WO-2006020609 A1 | 2/2006 |
| WO | 2006062788 | 6/2006 |
| WO | 2006063015 | 6/2006 |
| WO | WO-2006062788 A2 | 6/2006 |
| WO | WO-2006063015 A2 | 6/2006 |
| WO | 2006084821 | 8/2006 |
| WO | 2006086774 | 8/2006 |
| WO | WO-2006084821 A2 | 8/2006 |
| WO | WO-2006086774 A2 | 8/2006 |
| WO | 2007002053 | 1/2007 |
| WO | WO-2007002053 A2 | 1/2007 |
| WO | 2007044980 | 4/2007 |
| WO | 2007047200 | 4/2007 |
| WO | WO-2007044980 A2 | 4/2007 |
| WO | WO-2007047200 A1 | 4/2007 |
| WO | 2007053779 | 5/2007 |
| WO | WO-2007053779 A2 | 5/2007 |
| WO | 2007/075677 | 7/2007 |
| WO | WO-2007/075677 A2 | 7/2007 |
| WO | 2007099044 | 9/2007 |
| WO | WO-2007099044 A1 | 9/2007 |
| WO | 2007/126851 | 11/2007 |
| WO | WO-2007/126851 A2 | 11/2007 |
| WO | 2007138299 | 12/2007 |
| WO | 2007138313 | 12/2007 |
| WO | 2007140610 | 12/2007 |
| WO | WO-2007138299 A1 | 12/2007 |
| WO | WO-2007138313 A1 | 12/2007 |
| WO | WO-2007140610 A1 | 12/2007 |
| WO | WO-2008/004670 A1 | 1/2008 |
| WO | 2008021776 | 2/2008 |
| WO | 2008024810 | 2/2008 |
| WO | WO-2008021776 A2 | 2/2008 |
| WO | WO-2008024810 A2 | 2/2008 |
| WO | 2008048750 | 4/2008 |
| WO | WO-2008048750 A2 | 4/2008 |
| WO | 2008064092 | 5/2008 |
| WO | WO-2008064092 A2 | 5/2008 |
| WO | 2008075033 | 6/2008 |
| WO | WO-2008075033 A1 | 6/2008 |
| WO | 2008083313 | 7/2008 |
| WO | WO-2008083313 A2 | 7/2008 |
| WO | 2008093063 | 8/2008 |
| WO | 2008094984 | 8/2008 |
| WO | 2008095124 | 8/2008 |
| WO | WO-2008093063 A2 | 8/2008 |

(56) References Cited

FOREIGN PATENT DOCUMENTS

| | | |
|---|---|---|
| WO | WO-2008094984 A2 | 8/2008 |
| WO | WO-2008095124 A1 | 8/2008 |
| WO | 2008/113772 A1 | 9/2008 |
| WO | 2008107670 | 9/2008 |
| WO | WO-2008107670 A2 | 9/2008 |
| WO | 2008139458 | 11/2008 |
| WO | 2008139460 | 11/2008 |
| WO | WO-2008139458 A2 | 11/2008 |
| WO | WO-2008139460 A2 | 11/2008 |
| WO | 2008146021 | 12/2008 |
| WO | WO-2008146021 A1 | 12/2008 |
| WO | 2009006725 | 1/2009 |
| WO | WO-2009006725 A1 | 1/2009 |
| WO | 2009019437 | 2/2009 |
| WO | WO-2009019437 A1 | 2/2009 |
| WO | 2009097325 | 8/2009 |
| WO | WO-2009097325 | 8/2009 |
| WO | WO-2009097325 A1 | 8/2009 |
| WO | 2009125879 | 10/2009 |
| WO | WO-2009125879 A1 | 10/2009 |
| WO | 2009143255 | 11/2009 |
| WO | WO-2009143255 A1 | 11/2009 |
| WO | 2010023481 | 3/2010 |
| WO | 2010026414 | 3/2010 |
| WO | WO-2010023481 A1 | 3/2010 |
| WO | WO-2010026414 A1 | 3/2010 |
| WO | 2010076275 | 7/2010 |
| WO | WO-2010076275 A1 | 7/2010 |
| WO | 2010091133 | 8/2010 |
| WO | WO-2010091133 A2 | 8/2010 |
| WO | 2010/099850 | 9/2010 |
| WO | 2010100213 | 9/2010 |
| WO | WO-2010/099850 A1 | 9/2010 |
| WO | WO-2010100213 A1 | 9/2010 |
| WO | 2010127449 | 11/2010 |
| WO | WO-2010127449 A1 | 11/2010 |
| WO | WO-2011/014525 A2 | 2/2011 |
| WO | 2011/056888 A2 | 5/2011 |
| WO | 2011057065 | 5/2011 |
| WO | WO-2011057065 A1 | 5/2011 |
| WO | 2011/089206 A2 | 7/2011 |
| WO | 2012000871 | 1/2012 |
| WO | 2012000940 | 1/2012 |
| WO | WO-2012000871 A1 | 1/2012 |
| WO | WO-2012000940 A2 | 1/2012 |
| WO | 20121022771 A2 | 2/2012 |
| WO | 2012/080481 A1 | 6/2012 |
| WO | 2012/103140 | 8/2012 |
| WO | WO-2012/103140 A1 | 8/2012 |
| WO | 2012145685 | 10/2012 |
| WO | WO-2012145685 A1 | 10/2012 |
| WO | 2012164389 | 12/2012 |
| WO | 2012164394 | 12/2012 |
| WO | 2012164397 | 12/2012 |
| WO | WO-2012164389 A2 | 12/2012 |
| WO | WO-2012164394 A2 | 12/2012 |
| WO | WO-2012164397 A1 | 12/2012 |
| WO | 2013001378 | 1/2013 |
| WO | WO-2013001378 A2 | 1/2013 |
| WO | 2013034984 | 3/2013 |
| WO | 2013034986 | 3/2013 |
| WO | WO-2013034984 A2 | 3/2013 |
| WO | WO-2013034986 A2 | 3/2013 |
| WO | 2013065055 | 5/2013 |
| WO | WO-2013065055 A1 | 5/2013 |
| WO | 2014143815 | 9/2014 |
| WO | 2014144096 | 9/2014 |
| WO | WO-2014143815 A2 | 9/2014 |
| WO | WO-2014144096 A1 | 9/2014 |

OTHER PUBLICATIONS

"Office Action", dated Mar. 8, 2015, issued in related U.S. Appl. No. 13/269,750.

Australian Patent Application No. 2019202863, Examination Report No. 1, dated Sep. 13, 2019.

Canadian Patent Application No. 3021845, Examiner's Report, dated Aug. 19, 2019.

European patent application No. 12774589.1, Examination Report, dated Oct. 31, 2017.

European Search Report and Search Opinion Received for EP Application No. 19154409.7, dated Oct. 31, 2019, 9 pages.

Final Office Action, dated Jun. 1, 2015, issued in Related Japanese Patent Application No. 2011-510683 (counterpart to related U.S. Appl. No. 12/993,163).

International Application No. PCT/US09/44693, filed May 20, 2009, entitled, "Autoinjector System", Slate, et al.

International Patent Application No. PCT/US09/44693, Written Opinion of the International Searching Authority, dated May 20, 2009.

Japanese Patent Application No. 2018-188224, Notice of Reasons for Rejection, dated Aug. 5, 2019.

Michael Denzer et al., related copending U.S. Appl. No. 14/112,479, 371(c) dated Sep. 17, 2014.

Office Action received for European Patent Application No. 14765760.5, dated Jul. 9, 2019, 4 pages.

Search Report for Taiwan Patent Application No. 106100512, Office Action, dated Dec. 4, 2017.

U.S. Appl. filed Feb. 23, 2017, John B. Slate et al., U.S. Appl. No. 15/440,420.

U.S. Appl. filed Jul. 23, 2008, John B. Slate et al., U.S. Appl. No. 12/178,447

U.S. Appl. filed May 27, 2011, entitled, "Autoinjector System," of Slate et al., U.S. Appl. No. 12/993,163

U.S. Appl. filed May 27, 2016, John B. Slate et al., U.S. Appl. No. 15/167,068.

U.S. Appl. filed Oct. 10, 2011, John B. Slate et al., U.S. Appl. No. 13/269,750

Unpublished related U.S. Appl. No. 14/777,255.

U.S. Appl. No. 15/167,068, Nonfinal Office Action, dated Oct. 9, 2019.

U.S. Appl. No. 15/782,925, Final Office Action, dated Oct. 11, 2019.

Australian Patent Application No. 2014268140, Office Action, dated Sep. 2, 2016.

Australian Patent Application No. 2017200125, Examination Report No. 1, dated Sep. 18, 2017.

Canadian patent application No. 2724641, Examination Report, dated Dec. 15, 2016.

Canadian patent application No. 2724641, Examination Report, dated Sep. 29, 2017.

Canadian Patent Application No. 2724641, Office Action, dated Jun. 4, 2015.

Canadian patent application No. 2833748, Examination Report, dated Aug. 12, 2016.

Canadian patent application No. 2833748, Examination Report, dated May 2, 2017.

Canadian Patent Application No. 2833748, Office Action, dated Nov. 23, 2015.

European patent application No. 09751483.0, Extended Search Report, dated Aug. 1, 2013.

European Patent Application No. 09751483.0, Office Action, dated Apr. 10, 2015.

European patent application No. 09751483.0, Office Action, dated Aug. 1, 2016.

European Patent Application No. 09751483.0, Office Action, dated May 14, 2014.

European Patent Application No. 09751483.0, Office Action, dated Nov. 16, 2015.

European patent application No. 12774589.1, Extended Search Report, dated Feb. 23, 2015.

European Patent Application No. 12774589.1, Extended Search Report, dated Jul. 8, 2015.

European patent application No. 14763010.7, Extended Search Report and Opinion, dated Jan. 10, 2017.

European patent application No. 14763010.7, Partial Supplementary Search Report, dated Oct. 24, 2016.

(56) References Cited

OTHER PUBLICATIONS

European patent application No. 14765760.5, Extended Search Report, dated Jan. 11, 2017.
European patent application No. 14765760.5, Partial Supplementary Search Report, dated Oct. 24, 2016.
International Patent Application No. PCT/US2014/027950, International Preliminary Report on Patentability, dated Sep. 15, 2015.
International Patent Application No. PCT/US2014/028363, International Preliminary Report on Patentability, dated Sep. 15, 2015.
International Patent Application No. PCT/US09/44693, International Preliminary Report on Patentability, dated Nov. 23, 2010.
International Patent Application No. PCT/US09/44693, International Search Report, dated Jul. 21, 2009.
International Patent Application No. PCT/US2012/034535, International Preliminary Report on Patentability, dated Oct. 22, 2013.
International Patent Application No. PCT/US2012/34535, International Search Report and Written Opinion, dated Aug. 17, 2012.
International Patent Application No. PCT/US2014/027950, International Search Report and Written Opinion, dated Oct. 7, 2014.
International Patent Application No. PCT/US2014/028363, International Search Report and Written Opinion, dated Aug. 18, 2014.
Japanese Patent Application No. 2011-510683, Notice of Allowance, dated Oct. 5, 2015.
Japanese Patent Application No. 2011-510683, Office Action, dated Jul. 30, 2013.
Japanese Patent Application No. 2011-510683, Office Action, dated Jun. 30, 2014.
Japanese Patent Application No. 2014-021052, Final Office Action, dated Apr. 20, 2015.
Japanese Patent Application No. 2014-021052, Notice of Allowance, dated Aug. 24, 2015.
Japanese Patent Application No. 2014-021052, Office Action, dated Jan. 5, 2015.
Japanese Patent Application No. 2014-506591, Notice of Allowance, dated Oct. 3, 2016.
Japanese Patent Application No. 2014-506591, Office Action, dated Jan. 4, 2016.
Japanese Patent Application No. 2015-171851, Decision of Rejection, dated Feb. 6, 2017.
Japanese Patent Application No. 2015-186876, Office Action, dated Jul. 15, 2016.
Japanese Patent Application No. 2016-214237, Notice of Reasons for Rejection, dated Sep. 4, 2017.
Mexican Patent Application No. Mx/a/2010/012691, Office Action, dated Feb. 10, 2014.
Mexican Patent Application No. MX/a/2010/012691, Office Action, dated Sep. 24, 2014.
Taiwan Patent Application No. 103109332, Office Action, dated Aug. 22, 2016.
Taiwan Patent Application No. 103109475, Office Action, dated Aug. 26, 2016.
U.S. Appl. No. 12/123,888, Nonfinal Office Action, dated Dec. 22, 2010.
U.S. Appl. No. 12/123,888, Notice of Allowance, dated Jan. 12, 2012.
U.S. Appl. No. 12/123,888, Office Action, dated Apr. 8, 2010.
U.S. Appl. No. 12/123,888, Office Action, dated Jun. 8, 2011.
U.S. Appl. No. 12/123,888, Office Action, dated Oct. 5, 2009.
U.S. Appl. No. 12/178,447, Final Office Action, dated Mar. 30, 2010.
U.S. Appl. No. 12/178,447, Non-Final Office Action, dated Dec. 22, 2010.
U.S. Appl. No. 12/178,447, Nonfinal Office Action, dated Oct. 15, 2009.
U.S. Appl. No. 12/178,447, Notice of Allowance, dated Jun. 24, 2011.
U.S. Appl. No. 12/178,447, Notice of Allowance, dated Apr. 6, 2011.
U.S. Appl. No. 12/454,531, Non-Final Office Action, dated Sep. 13, 2013.
U.S. Appl. No. 12/993,163, Final Office Action, dated Feb. 22, 2016.
U.S. Appl. No. 12/993,163, Non-Final Office Action, dated Dec. 27, 2013.
U.S. Appl. No. 12/993,163, Non-Final Office Action, dated Jul. 28, 2016.
U.S. Appl. No. 12/993,163, Office Action, dated May 8, 2015.
U.S. Appl. No. 13/269,740, Restriction Requirement, dated Apr. 2, 2013.
U.S. Appl. No. 13/269,740, Office Action, dated May 20, 2013.
U.S. Appl. No. 13/269,750, Final Office Action, dated Dec. 26, 2013.
U.S. Appl. No. 13/269,750, Final Office Action, dated Oct. 18, 2016.
U.S. Appl. No. 13/269,750, Non Final Office Action, dated May 3, 2016.
U.S. Appl. No. 13/269,750, Non-Final Office Action, dated Aug. 21, 2014.
U.S. Appl. No. 13/269,750, Non-final Office Action, dated Jun. 21, 2013.
U.S. Appl. No. 13/269,750, Notice of Allowance, dated Feb. 8, 2017.
U.S. Appl. No. 13/269,750, Office Action, dated Aug. 10, 2015.
U.S. Appl. No. 13/269,750, Office Action, dated Mar. 12, 2015.
U.S. Appl. No. 13/269,750, Office Action, dated Nov. 18, 2015.
U.S. Appl. No. 13/454,531, Final Office Action, dated Sep. 23, 2016.
U.S. Appl. No. 13/454,531, Non-Final Office Action, dated Dec. 28, 2012.
U.S. Appl. No. 13/454,531, Non-Final Office Action, dated Mar. 17, 2016.
U.S. Appl. No. 13/454,531, Notice of Allowance, dated Oct. 5, 2015.
U.S. Appl. No. 13/454,531, Office Action, dated Apr. 21, 2015.
U.S. Appl. No. 13/454,531, Office Action, dated Oct. 7, 2014.
U.S. Appl. No. 14/112,479, Final Office Action, dated Feb. 27, 2017.
U.S. Appl. No. 14/112,479, Nonfinal Office Action, dated Jul. 12, 2017.
U.S. Appl. No. 14/112,479, Nonfinal Office Action, dated Jul. 29, 2016.
U.S. Appl. No. 29/548,507, Denzer et al., filed Dec. 14, 2015.
U.S. Appl. No. 29/548,508, Denzer et al., filed Feb. 14, 2015.
Australian Patent Application No. 2017202210, Examination Report No. 1, dated Oct. 25, 2018.
Canadian Patent Application No. 2724641, Office Action, dated May 27, 2019.
Japanese Patent Application No. 2017-089529, Notice of Reasons for Rejection, dated Apr. 2, 2018.
Japanese Patent Application No. 2017-089529, Notice of Reasons for Rejection, dated Sep. 14, 2018.
U.S. Appl. No. 15/167,068, Final Office Action, dated Apr. 24, 2019.
U.S. Appl. No. 15/167,068, Nonfinal Office Action, dated Oct. 18, 2018.
Australian Patent Application No. 2018253467, Examination Report No. 1, dated Dec. 6, 2019.
European Patent Application No. 19191313.6, European Search Report, dated Dec. 16, 2019.
Examiner initiated interview summary, U.S. Appl. No. 15/782,951, dated Oct. 11, 2019, 2 pages.
Japanese Patent Application No. 2016-502669, Notice of Reasons for Rejection, dated Jan. 14, 2020., Jan 14, 2020.
Japanese Patent Application No. 2018-086731, Decision of Rejection, dated Feb. 3, 2020.
Japanese Patent Application No. 2018-228060, Notice of Reasons for Rejection, dated Oct. 21, 2019.
Notice of Allowance, U.S. Appl. No. 15/782,951, dated Oct. 11, 2019, 9 pages.
U.S. Appl. No. 15/167,068, Nonfinal Office Action, dated Feb. 14, 2020.
Japanese Patent Application No. 2019-070580, Notice of Reasons for Rejection, dated Feb. 25, 2020.
U.S. Appl. No. 16/026,294, Nonfinal Office Action, dated Mar. 18, 2020.

(56) References Cited

OTHER PUBLICATIONS

Australian Patent Application No. 2009249027, Notice of Acceptance, dated Aug. 7, 2014.
Australian Patent Application No. 2009249027, Office Action, dated Jul. 24, 2013.
Australian Patent Application No. 2012245231, First Examination Report, dated Oct. 19, 2015.
Australian Patent Application No. 2012245231, Notice of Allowance, dated Oct. 4, 2016.
Australian Patent Application No. 2012245231, Office Action, dated Jul. 5, 2016.
Australian Patent Application No. 2014268139, Office Action, dated Jul. 19, 2016.
Australian Patent Application No. 2014268140, Office Action, dated Jul. 22, 2016.
Canadian Patent Application No. 3021845, Examiner's Report, dated May 7, 2020.
U.S. Appl. No. 15/782,951, Notice of Allowance, dated May 20, 2020.
U.S. Appl. No. 15/167,068, Notice of Allowance, dated Jul. 2, 2020.
U.S. Appl. No. 16/026,294, Final Office Action, dated Jul. 30, 2020.

\* cited by examiner

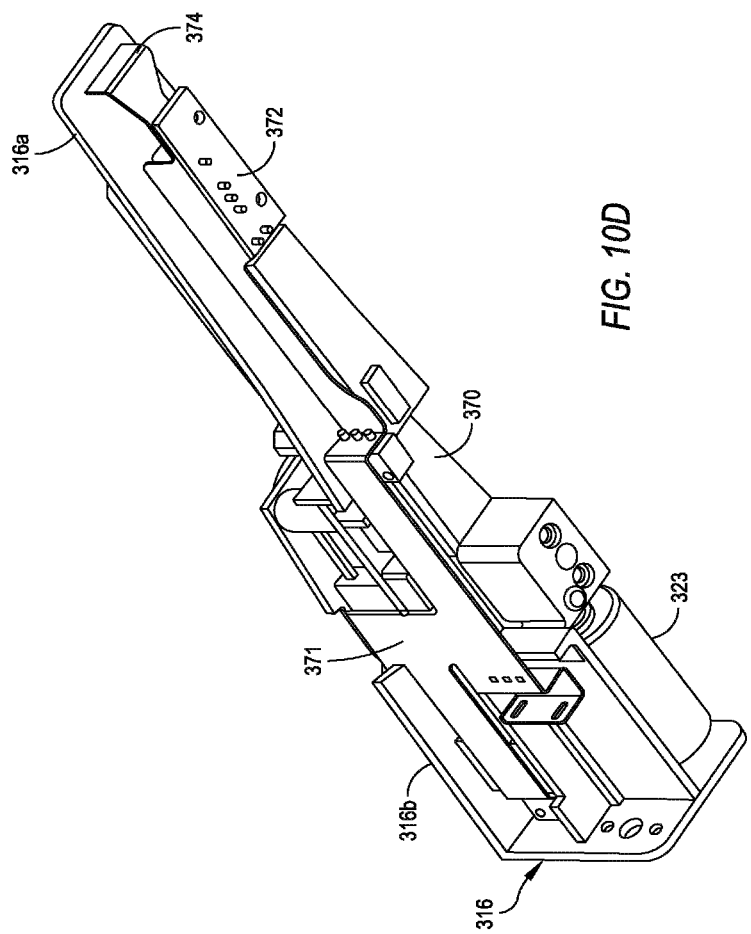

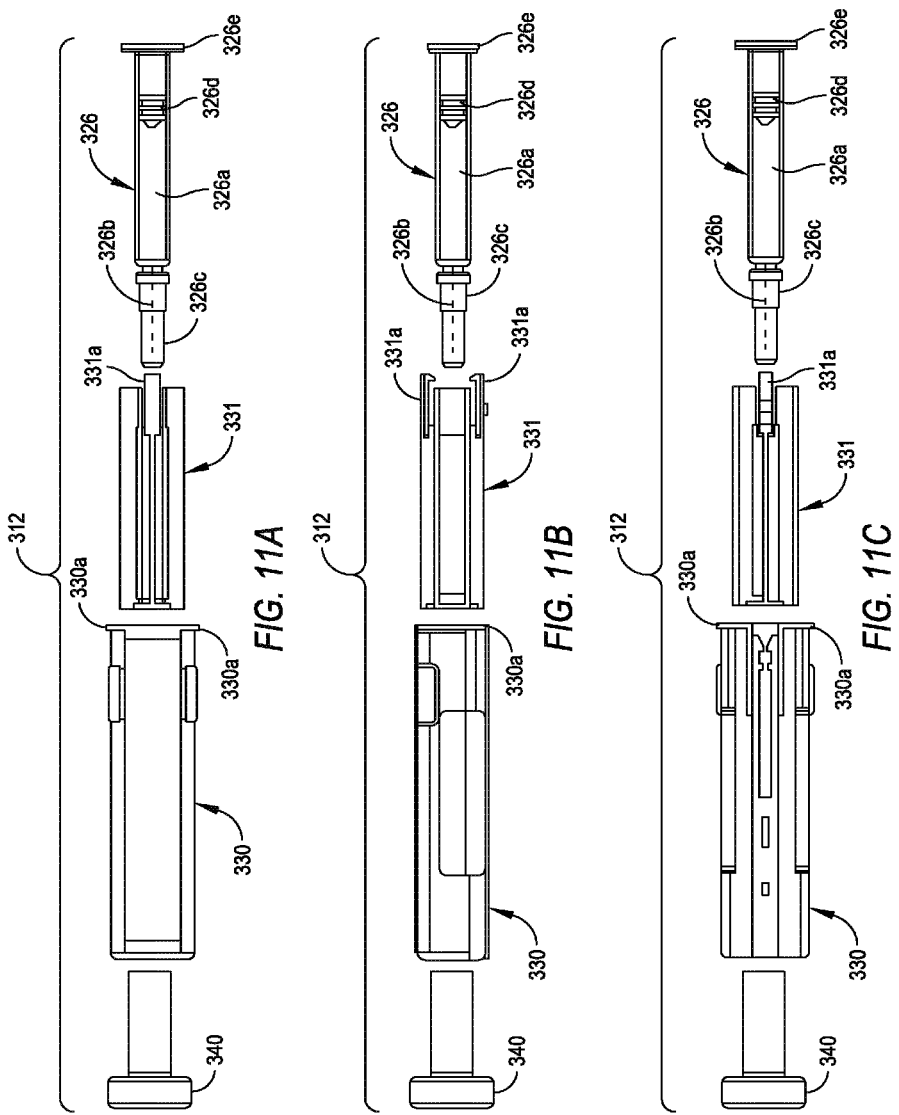

| Average of delta t | | Injector | | | |
|---|---|---|---|---|---|
| solution viscosity (cp) | speed setting | CM2-1 | CM2-2 | CM2-3 | Grand Total |
| 1 | low(0) | 4.9 | 5.0 | 5.0 | 4.9 |
| | med(28) | 3.5 | 3.6 | 3.5 | 3.5 |
| | fast(44) | 2.9 | | | 2.9 |
| 19 | low(0) | 8.1 | 9.6 | 9.3 | 9.0 |
| | med(28) | 6.4 | 6.7 | 6.3 | 6.5 |
| | fast(44) | 4.4 | | | 4.4 |
| 29 | low(0) | 11.8 | | | 11.8 |
| | med(28) | 7.5 | | | 7.5 |

*FIG. 15*

AUTOINJECTOR SYSTEM

RELATED APPLICATIONS

This is a Divisional of U.S. application Ser. No. 12/993,163, filed on May 27, 2011, which is the US National phase of PCT/US09/44693, filed May 20, 2009, and claims the benefit of priority as a continuation-in-part of U.S. application Ser. No. 12/123,888, filed May 20, 2008 and as a continuation-in-part of U.S. application Ser. No. 12/178,447, filed Jul. 23, 2008, the entire contents of each of these applications are incorporated herein by reference.

FIELD

The present disclosure relates to a system and method for injecting medicaments into a patient from a hypodermic syringe. More particularly, the present disclosure relates to an auto-injector and a cassette useable with the auto-injector, which conceals the injection needle of a hypodermic syringe before and after an injection.

BACKGROUND

Pre-filled hypodermic syringes provide several advantages for the home-use market. These advantages include that pre-filled syringes may be prepared for each medicament with exactly the required dosage. Further, they are easily operated, by merely advancing the stopper of the syringe. Aside from the costs of the particular medication that is being used, pre-filled syringes are also economically manufactured. Consequently, all these advantages make pre-filled syringes commercially appealing.

Nevertheless, pre-filled syringes also have a significant drawback in the marketplace. Specifically, many users are either frightened by an exposed needle or feel they are inherently incapable of performing an injection. Because of aversions to exposed needles, as well as the many health and safety issues that may be involved, various types of injectors and other devices have been developed for the specific purpose of concealing needles from the user and automating the injection task to assist the user in performing the injection.

In order to inject a fluid medicament into a patient whets using a hypodermic syringe, generally three separate and distinct tasks must be performed. These are: 1) insertion of the needle into the patient; 2) injection of the fluid medicament from the syringe into the patient; and 3) withdrawal of the needle after the injection has been completed. For each task, the magnitude and direction of forces on the syringe, as well as the location of their application, are different from the other tasks. For instance, compare the task of inserting the needle, with the task of injecting the fluid medicament. Insertion of the needle requires that only minimal forces be applied on the syringe, and that they be applied for only a very short period of time. On the other hand, injection of the medicament requires a much greater force be applied. Further, this force must be applied on the plunger of the syringe for what will typically be a relatively longer period of time. In comparison with both of these tasks, needle withdrawal requires the application of a force in the opposite direction. These, and other similar considerations, become important when the injection process is to be automated.

Springs for generating forces on a syringe in an automated process have been used heretofore for various purposes. A characteristic of springs, however, is that the magnitude and direction of a spring force are not variable. Consequently, springs do not lend themselves for so-called multi-tasking operations. This is particularly so where precise control over a syringe injection operation is required, and different magnitude forces are sequentially required in the same direction (e.g. needle insertion and medicament injection). This can be particularly problematic in situations where it may be desirable to use the same device, at different times, to inject different medications, with different fluid viscosities.

In addition to the mechanical considerations mentioned above, the design of an auto-injector also requires user-friendly considerations. In particular, it is desirable that the injection needle of a syringe be operationally concealed from the view of a user. Preferably, this concealment may be maintained before, during and after an injection procedure. Further, it is desirable that operation of the syringe be limited to only those times when the syringe is properly positioned for an injection.

Accordingly, an improved medicament injection system is needed, which hides the syringe needle during use, is capable of accommodating different force requirements during an injection procedure, is relatively easy and inexpensive manufacture, and is easy to use.

SUMMARY

In accordance with the present disclosure, a system for injecting fluid medicaments into a patient from a pre-filled hypodermic syringe, employs a cassette that is pre-loaded with the pre-filled syringe. For this combination, the hypodermic syringe can be loaded into the cassette during manufacture, or be subsequently loaded by a contract service provider. In either case, the syringe needle is concealed inside the cassette and hidden from the view of the end-user. Importantly, the only preparation required by the end-user (e.g. the patient that is to self-administer the fluid medicament) is to mount the cassette onto a drive mechanism.

Structurally, the system of the present disclosure envisions a pre-filled syringe that will have a needle, and it will have a stopper for expelling the fluid medicament from the syringe through the needle. Further, the pre-filled syringe will be firmly held on the cassette in a position where the syringe needle is concealed and hidden from view. As envisioned for the present disclosure, the pre-filled hypodermic syringe can be firmly held in the concealed position, in any of several different ways. These include, the use of a latching mechanism, an adhesive, or a flexible abutment.

Once the cassette has been loaded with the pre-filled hypodermic syringe, the cassette can be engaged with a drive mechanism. In detail, the drive mechanism includes two separate motors that perform two different functions. A first motor is provided for engaging the syringe in its concealed position where its needle is hidden. With this engagement, the first motor then moves the syringe and its needle from the concealed position and into an exposed position where the needle is extended for insertion into the patient. While the needle is inserted into the patient, a second motor is provided for pushing the stopper on the syringe to expel fluid medicament from the syringe. After the injection has been completed, the first motor then withdraws the syringe and its needle back into the concealed position. Importantly, after it has been withdrawn the syringe is again firmly held in the concealed position, inside the cassette. Thus, the needle remains hidden from view at all times during an injection procedure. Further, as noted above, the syringe is firmly held inside the cassette to insure the syringe needle does not inadvertently extend from the cassette.

In operation, an end-user mounts a pre-loaded cassette on the drive mechanism. The end-user then removes a protective cover from the syringe needle and positions the system at a site where an injection is to be made. A button on the system is then pushed to activate the drive mechanism for an injector procedure. After the injection has been completed, the cassette, with its now empty syringe, can be removed from the drive mechanism and discarded.

In accordance with the present disclosure an autoinjector system includes a disposable cassette that operates in combination with a reusable injector. Prior to an engagement of the cassette with the injector, however, a pre-filled syringe is mounted and latched onto the cassette. When latched, the syringe is held on the cassette in a home position. For the present disclosure, this pre-filled syringe may be of any type syringe well-known in the pertinent art that has a fluid chamber with an injection needle at its distal end, and a plunger that can be advanced into the fluid chamber. When the cassette, with syringe, is engaged with the injector, the system is ready for use.

Operation of the system of the present disclosure requires two separate motors that are individually mounted on the injector. Though they are mechanically independent of each other, the respective operations of these two motors must be coordinated. Specifically, a first motor is used to effect movements of the entire syringe assembly (i.e. syringe chamber, injection needle and plunger are all moved together). On the other hand, a second motor is employed to advance the plunger into the fluid chamber for performing an injection of a fluid medicament.

In a duty cycle of the system, the first motor moves a drive rod into engagement with the syringe. With this engagement, the drive rod also releases the latch that otherwise holds the syringe in the home position. After the syringe has been released, the first motor then advances the syringe in a distal direction on the cassette. This movement inserts the injection needle into a patient. Further, the first motor can be used to abruptly stop the needle when a specified needle depth has been achieved. The first motor can then be used to help stabilize the needle during an injection of the medical medicament from the syringe.

As mentioned above, the injection of medical medicament from the syringe is accomplished using the second motor. In detail, once the needle has been properly inserted into the patient, the second motor moves a pusher to urge against the plunger of the syringe to advance the plunger into the fluid chamber of the syringe. Importantly, the second motor can be programmed to advance the plunger into the fluid chamber at a predetermined rate(s) for compliance with an injection protocol.

After the injection has been completed, the second motor withdraws the pusher. The first motor is then used again. Specifically, the first motor is now used to withdraw the injection needle from the patient, and to return the syringe to the home position on the cassette, where it is re-latched onto the cassette. The cassette can then be removed from the injector and discarded.

In order to control the concerted operations of the first and second motors, the system includes a microcomputer that is mounted on the injector. Importantly, the microcomputer operates the motors with different forces, and at different speeds for different purposes. More specifically, the first motor must operate quickly to insert the needle (e.g. about 0.1 meters/second (m/s) to 1.0 m/s), but it does not require much force to do so. Similarly, needle withdrawal by the first motor requires a minimal force. Unlike the first motor, however, the second motor will typically be required to generate greater forces for the injection of fluid medicament. And, accordingly, it will also typically operate at slower speeds. Further, and most importantly, different injections (i.e. advancements of the syringe plunger by the second motor) may require different injection rates. Thus, the second motor requires speed control provided by the microcomputer.

Together with the components mentioned above, the system of the present disclosure may employ a capacitance skin sensor of a type well known in the pertinent art. If used, such a sensor will allow the user to ascertain whether the system has been properly positioned for an injection. In detail, a metal foil is positioned at the extreme distal end of the injector to establish a capacitance signal whenever the foil is in contact with a skin surface of the patient. The function of this signal is actually two-fold. First, it can be used to prevent initial operation, if the system is not properly positioned. And, second, it can be used to interrupt operation of the system, if it becomes improperly positioned during an injection.

Further disclosed herein is a system for injecting a medicament into a patient. The system comprises an injector and a medicament cassette. The medicament cassette comprises a housing, a sleeve movable in the housing between first and second positions, and a syringe comprising a chamber for containing a medicament and an injection needle extending from the syringe chamber. The syringe chamber is at least partially disposed in the sleeve and the injection needle has a skin penetrating end opposite the syringe chamber. The skin penetrating end is disposed within the housing when the sleeve is in the first position and the skin penetrating end extends out from the housing when the sleeve is in the second position. The injector comprises a surface for removably mounting the cassette thereon, and a motor driven link having a first end engageable with a portion of the sleeve when the cassette is mounted on the surface. The link is provided for moving the sleeve from the first position to the second position.

Still further disclosed herein is a system for injecting a medicament. The system comprises an injector and a medicament cassette comprising a syringe for containing a medicament. The injector comprises a plunge rod for expelling the fluid medicament from the syringe, a motor for driving the plunge rod, and a switch operatively coupled to the motor, for allowing a user to set the motor to one of a plurality of different speeds. The plurality of different speeds correspond to a plurality of different injection rates of the system.

Also disclosed herein is a medicament cassette for an autoinjector. The medicament cassette comprises a housing, a sleeve movable in the housing between first and second positions, and a syringe comprising a chamber for containing a medicament and an injection needle extending from the syringe chamber. The syringe chamber is at least partially disposed in the sleeve. The injection needle has a skin penetrating end opposite the syringe chamber, the skin penetrating end disposed within the housing when the sleeve is in the first position and the skin penetrating end extending out from the housing when the sleeve is in the second position. A portion of the sleeve engages a drive link of the autoinjector, when the cassette is mounted on or in the autoinjector.

Further disclosed herein is an injector for injecting a medicament into a patient. The injector comprises a surface for removably mounting a cassette thereon, the cassette having disposed therein a sleeve holding a syringe containing the medicament and a motor driven link having a first end engageable with a portion of the cassette when the cassette is mounted on the surface, the link for moving the sleeve from the first position to the second position.

Also disclosed is a system for injecting a medicament into a patient, comprising an injector and a medicament cassette. The medicament cassette comprises a housing and a syringe comprising a chamber for containing a medicament and an injection needle extending from the syringe chamber, the injection needle having a skin penetrating end opposite the syringe chamber, the skin penetrating end disposed within the housing when the syringe is in a first position and the skin penetrating end extending out from the housing when the syringe is in a second position. The injector comprises a surface for removably mounting the cassette thereon, a motor driven link having a first end engageable with a portion of the syringe when the cassette is mounted on the surface, the link for moving the syringe from the first position to the second position.

Also disclosed is a medicament cassette for an autoinjector, comprising a housing anti a syringe. The syringe comprises a chamber for containing a medicament and an injection needle extending from the syringe chamber, the injection needle having a skin penetrating end opposite the syringe chamber, the skin penetrating end disposed within the housing when the syringe is in a first position and the skin penetrating end extending out from the housing when the syringe is in a second position. A portion of the syringe engages a drive link of the autoinjector, when the cassette is mounted on or in the autoinjector.

Further disclosed is a system for injecting a medicament into a patient, comprising an injector and a medicament cassette. The injector comprises a surface for removably mounting the cassette thereon and a motor driven link having a first end for operating the cassette in a needle injection mode.

Further disclosed is a system for injecting a medicament, comprising an injector and a medicament cassette. The injector comprises a plunge rod for expelling a fluid medicament from a syringe, a motor for driving the plunge rod, and a switch operatively coupled to the motor, for allowing a user to select one of a plurality of different medicament injection rates of the system.

BRIEF DESCRIPTION OF THE DRAWINGS

Reference will now be made in detail to the aspects of the present disclosure, examples of which are illustrated in the accompanying drawings, wherein like reference numerals refer to like elements throughout.

FIG. 10D is a perspective bottom view of the internal frame shown in FIG. 10A with autoinjector control components attached thereto.

FIG. 11A is an exploded top view of a cassette similar to the one shown in FIG. 9.

FIG. 11B is an exploded side view of a cassette similar to the one shown in FIG. 9.

FIG. 11C is an exploded bottom view of a cassette similar to the one shown in FIG. 9.

FIG. 15 is table showing injection rates of three different samples of an autoinjector system set at low medium and high delivery motor speed settings for solutions of three different viscosities in centipoise.

DETAILED DESCRIPTION

Figure 1:
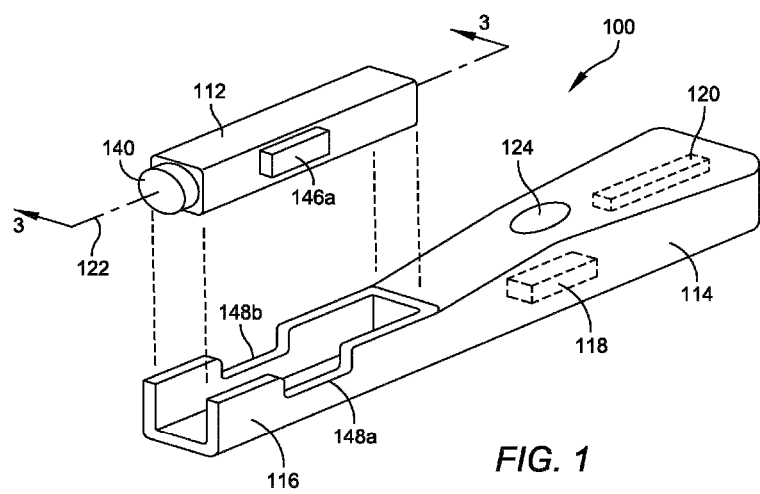
FIG. 1 is a perspective view of an exemplary embodiment of an autoinjector system for injecting a medicament into a patient.

Referring to FIG. 1, an exemplary embodiment of an autoinjector system for injecting a medicament into a user/patient (a user of the system or another person or animal) is shown and is designated by reference numeral 100. The system 100 generally includes a disposable cassette 112 and a re-usable drive mechanism or autoinjector 114. The autoinjector 114 includes a cradle 116 that is dimensioned to receive and hold the cassette 112 on the autoinjector 114. The autoinjector 114 includes a first (injection) motor 118 (shown in phantom) and a section (delivery) motor 120 (also shown in phantom). The motors 118 and 120 may comprise any suitable, well known type of motor including without limitation, stepper motors and reluctance motors. The motors 118 and 120 each includes a drive system for converting the rotary motion of the motor to linear motion. Such drive systems include without limitation, lead screw/ worm gear drive systems, rack and pinion drive systems, and any other linear drive or transmission system which enables the motors 118 and 120 to individually exert axially directed forces on contents of the cassette 112. These forces will need to be directed substantially along the axis 122. Activation of the motors 118 and 120 for the generation of these forces is accomplished by manipulation of a button 124 provided with the autoinjector 114.

Figure 2:
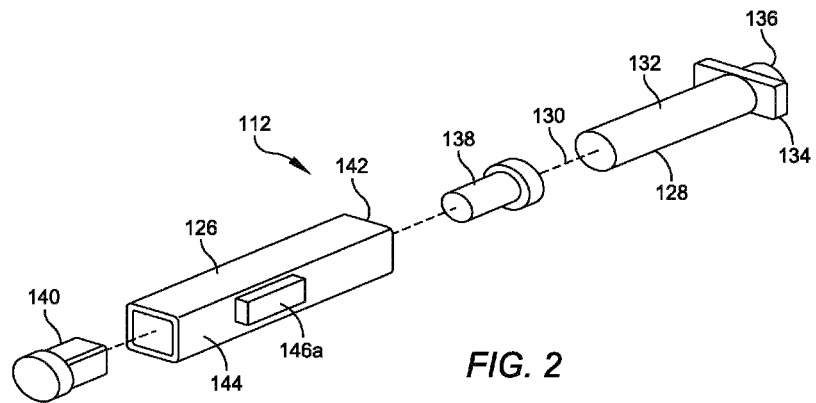
FIG. 2 is an exploded perspective view of a cassette of the autoinjector system of FIG. 1 with a pre-loaded, pre-filled hypodermic syringe.

Referring to FIG. 2, the cassette 112 comprises a housing 126 having hollow, tubular shaped structure for holding a hypodermic syringe 128 comprising an injection needle 130 that is affixed to the distal end of a fluid chamber 132. A conventional finger grip 134 is provided at the proximal end of the fluid chamber 132. Also, a stopper or plunger 136 is disposed in the proximal end of the fluid chamber 132 to expel fluid medicament from the fluid chamber 132 through the needle 130. A protective cover 138 may be provided to cover the needle 130 when system 100 is not in operational use, and a cap 140 is employed to grip the protective cover 138.

Prior to an operation of the system 100, the cassette 112 is pre-loaded with the syringe 128, which has been pre-filled with an appropriate dose of the desired medicament (e.g., a fluid medicament). Before pre-loading the cassette 112, the protective cover 138 is positioned over the needle 130 on syringe 128. The pre-filled syringe 128 is then inserted into the housing 126 through its proximal end 142. The cap 140 can then be inserted through the distal end 144 of the housing 126 to engage the cap 140 with the protective cover 138.

The cassette 112 (pre-loaded with the pre-filled syringe 128) may be mounted on the autoinjector 114, as shown in FIG. 1, by merely inserting the cassette 112 into the cradle 116 of the autoinjector. When inserted, the opposing protrusions (only protrusion 146a is shown) formed on the housing 126 of the cassette 112 engage with respective recesses 148a and 148b to stabilize the cassette 112 on autoinjector 114.

Figure 3A:
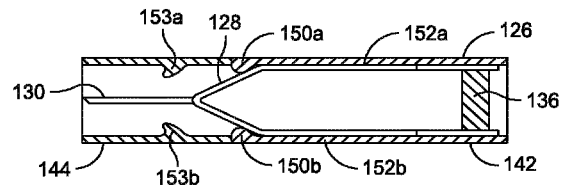
FIG. 3A is a sectional view of the pre-loaded cassette, as seen along the line 3-3 of FIG. 1, with the pre-filled hypodermic syringe in a needled concealed (proximal) position.
Figure 3B:
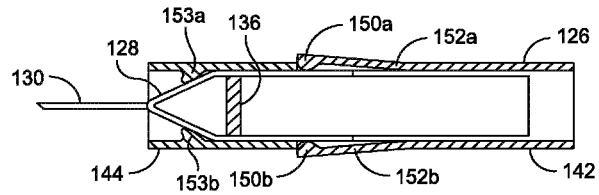
FIG. 3B is a sectional view of the pre-loaded cassette shown in FIG. 3A with the syringe in a needled extended (distal) position after drug delivery.

In one exemplary embodiment, as shown in FIG. 3A, the pre-filled syringe is firmly held inside the cassette 112 with the injection needle 130 of the syringe 128 concealed inside the cassette 112 and thereby hidden from the user/patient's view (a needle concealed position or proximal position) by opposing bumps 150a and 150b formed on inner surfaces of resilient arms 152a and 152b, respectively, of the housing 126 of the cassette 112. The bumps 150a and 150b firmly hold the syringe 128 in a home position (the needle concealed position) until resilient arms 152a and 152b are flexed outwardly by an axial force exerted by the syringe 128, as the drive system of the first motor 118 pushes the syringe 128 through the housing 126 of the cassette 112 to move the injection needle 130 from the needle concealed (proximal) position into a needle extended (distal) position, as shown in FIG. 3B. In this distal position, the syringe 128 is retained in the cassette 112 by stops 153a and 153b provided on inner surfaces of the cassette housing 126, while the injection needle 130 extends from the cassette housing 126 for insertion into a user/patient.

In one exemplary embodiment, the drive system of the first motor 118 engages the syringe 128 in a manner that allows the first motor 118 to retract the syringe 128 and thus the injection needle 130 from the extended (distal) position, thereby returning the injection needle 130 to its concealed (proximal) position with the syringe 128 firmly held in the housing 126 in the home position by the bumps 150a and 150b and the resilient arms 152a and 152b.

In an alternative embodiment, a single motor may be used in place of the first and second motors 118 and 120. The use of the single motor requires an appropriate drive or transmission which is capable of converting the rotary motion of the motor to linear motion and selectively applying the linear motion to the syringe 128 or the stopper 136.

Figure 4:
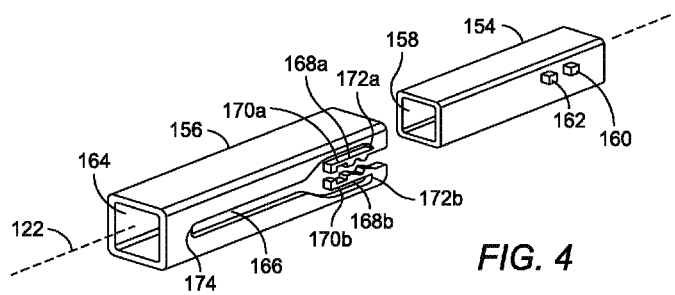
FIG. 4 is an exploded perspective view of another embodiment of the cassette.

FIG. 4 shows an alternate embodiment of the cassette 112, which includes an inner sleeve 154 and an housing 156. The inner sleeve 154 is a hollow, substantially tube-shaped structure defining a lumen 158. Formed on the outer surface of the inner sleeve 154 is a proximal projection 160 and a distal projection 162 that are axially aligned with each other. The housing 156 defines a lumen 164 and an axially aligned slot 166. Resilient arms 168a and 168b are formed on the housing 156 and are positioned to extend toward the proximal open end of the slot 166. The resilient arms 168a and 168b are respectively formed with detents 170a and 170b and ramps 172a and 172b. The resilient arms 168a and 168b and their corresponding detents 170a and 170b and ramps 172a and 172b define a latch mechanism.

The cassette of FIG. 4 is be pre-loaded with the syringe 128, according to one exemplary embodiment, by inserting the inner sleeve 154 into the lumen 164 of the housing 156 so that the proximal projection 160 on the inner sleeve 154 is positioned and held in the detents 170a and 170b of the resilient arms 168a and 168b, and then inserting the hypodermic syringe 128 into the lumen 158 of the inner sleeve 154. This places the injection needle 130 of the syringe 128 in the concealed (proximal) position within the cassette 112. Subsequently, movement of the syringe 128 through the housing 156, which moves the injection needle 130 from the needle concealed (proximal) position to the needle extended (distal) position is accomplished by the drive system of the first motor 118. In one exemplary embodiment, the drive system of the first motor 18 may include a bar (not shown) that pushes against the proximal projection 160 of the inner sleeve 154, thereby causing the arms 168a and 168b to spread and therefore, release the proximal projection 160 from their grasp. The inner sleeve 154, with syringe 128 firmly held therein, may then be moved in a distal direction through the lumen 164 of the housing 156. This distal movement continues until the distal projection 162 contacts an end abutment 174 of the slot 166. The injection needled 130 of the syringe 128 is now in the needled extended (distal) position. Subsequently, the drive system bar of the first motor 118 may be used to apply a pulling force on the proximal projection to withdraw the inner sleeve 154 in a proximal direction through the lumen 164 of the housing 156. This proximal movement continues until the proximal projection 160 on inner sleeve 154 again engages with the detents 170a and 170b, thereby returning the syringe 128 to the home position and thus placing the injection needle 130 into the corresponding needle concealed (proximal) position.

Figure 5:
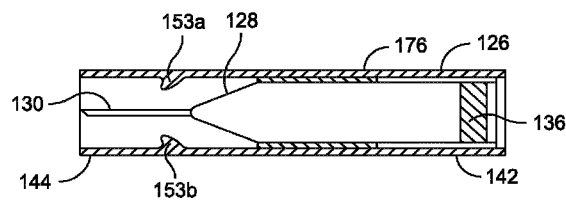
FIG. 5 is a sectional view of an alternate embodiment of the pre-loaded cassette, as seen along the line 3-3 in FIG. 1.

FIG. 5 shows yet another embodiment of the cassette 112. In this embodiment, an adhesive 176 is disposed on the inner surface of the housing 126 to firmly hold the syringe 128 in the needle concealed (proximal) position. The adhesive 176, or a similar type of restraining element, can be used either directly between the syringe 128 and the housing 126 of the cassette 112, as shown in FIG. 5. The adhesive 176 selectively releases the syringe 128 and then re-adheres to the syringe 28 in response to the push and pull forces exerted on the syringe 128 by the drive system of the first motor 118.

In one exemplary method of operation of the system 100, a pre-loaded cassette 112 is positioned in the cradle 116 of the autoinjector 114, which engages the syringe 128 (FIGS. 3A-3B and FIG. 5) or the proximal projection 160 of the inner sleeve 154 of the cassette 112 (FIG. 4) with the linear drive system of the first motor 118. Prior to an injection, the cap 140 is removed from the cassette 112. Because the cap 140 is attached to the protective cover 138 covering the needle 130 of the syringe 128, the protective cover 138 is also removed. The system 100 is now ready for an injection.

With the system 100 positioned at an injection site (not shown), the button 124 on autoinjector 114 is depressed. Depression of the button 124 causes the linear drive system of the first motor 118 to apply a pushing force to the syringe 128 (FIGS. 3A-3B and FIG. 5) or the proximal projection 160 of the inner sleeve 154 of the cassette 112 (FIG. 4), to move the syringe 128 from the home position where the injection needle 130 is in the needle concealed (proximal) position to an inject position where the injection needled 130 is in the needle extended (distal) position, thereby causing the needle 130 of syringe 128 to penetrate into tissue of the user/patient for an injection. At this time, the linear drive system of the second motor 120 pushes on the stopper 136 of the syringe 128 to expel medicament from the fluid chamber 132 of the syringe 128. After an injection has been completed, the first motor 118 is again activated to apply a pulling force to the syringe 128 (FIGS. 3A-3B and FIG. 5) or the proximal projection 160 of the inner sleeve 154 of the cassette 12 (FIG. 4), to withdraw the syringe 128 from the inject position where the injection needle 130 is in the needle extended (distal) position to the home position, where the injection needle 130 is in the needle concealed (proximal) position. The cassette 112, along with the expended syringe 128, can then be removed from the cradle 116 of the autoinjector 114 and discarded.

Figure 6:
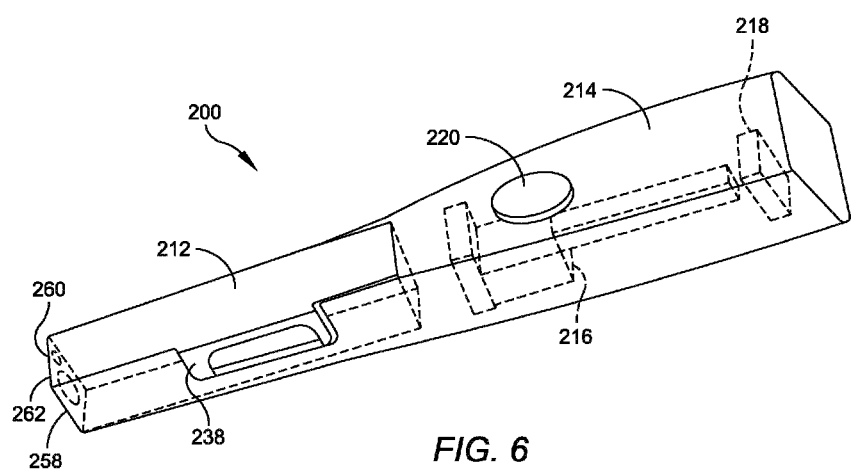
FIG. 6 is a perspective view of another exemplary embodiment of the autoinjector system showing the cassette engaged with the autoinjector.

FIG. 6 shows another exemplary embodiment of the autoinjector system designated by reference numeral 200. As shown, the system 200 generally includes a disposable cassette 212 and a re-useable autoinjector 214. Further, as shown in phantom in FIG. 6, a motor/drive system 216 and a microcomputer or controller 218 are mounted inside the autoinjector 214. The microcomputer 218 is activated by depressing a button 220 on the autoinjector 214. When activated, the microcomputer 218 controls the operation of the motor/drive system 216 for its interaction with the cassette 212.

Figure 7:
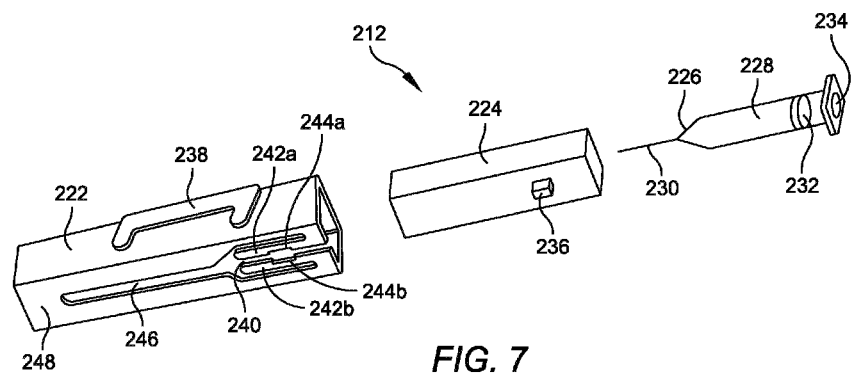
FIG. 7 is an exploded perspective view of the cassette of the autoinjector system of FIG. 6 and its component elements.

As shown in FIG. 7, the cassette 212 includes a housing 222, a inner sleeve 224 and a hypodermic syringe 226 including a fluid chamber 228 for holding a medicament, an injection needle 230, and a plunger 232 that is moveable within the fluid chamber 228 to expel medicament from the chamber 228 through the injection needle 230. The syringe 226 is formed with an orifice 234 that allows for contact with the plunger 232. The syringe 226 is fixedly joined with the inner sleeve 224 and this combination (i.e. syringe 226 and inner sleeve 224) is incorporated with the housing 222 to establish the cassette 212.

Still referring to FIG. 7, the inner sleeve 224 includes a projection or protrusion 236. The housing 222 is formed with a fixation member 238 that is dimensioned for engagement with the autoinjector 214 (FIG. 6). The fixation member 238 engages with the autoinjector 214 to position the cassette 212 in an operational alignment with the motor/drive system 216. The cassette 212 may be fixedly held on the autoinjector 214 during an operation duty cycle of the system 200, and selectively removed from the autoinjector 214 after its use.

As shown in FIG. 7, the housing 222 is formed with a latch mechanism 240. The latch mechanism 240 includes a pair of opposed, resilient arms 242a and 242b that are respectively formed with detents 244a and 244b. As shown, the resilient arms 242a and 242b extend toward the proximal end of a slot 246 that extends along the side 248 of the housing 222.

When assembled, the cassette 212 forms and integral unit and is intended for use only so long as there is medicament in the fluid chamber 228 of the syringe and, it is thereafter disposable. Prior to assembly, the fluid chamber 228 of the syringe 226 will be pre-filled with a defined dose of medicament. The pre-filled syringe 226 is then inserted into the inner sleeve 224 where it is fixedly held. Movements of the inner sleeve 224 will thus result in a corresponding movement of the syringe 226. The combination (i.e. syringe 226 and inner sleeve 224) is then joined with the housing 222. When so joined, the protrusion 236 on inner sleeve 224 fits in the detents 244a and 244b between the resilient arms 242a and 242b. Accordingly, the injection needle 230 of the syringe 226 is held inside and concealed in the housing 222 of the cassette 212 in a needle concealed (proximal) position. In this configuration, the cassette 212 may be installed in or onto the autoinjector 214 substantially as shown in FIG. 6.

Figure 8A:
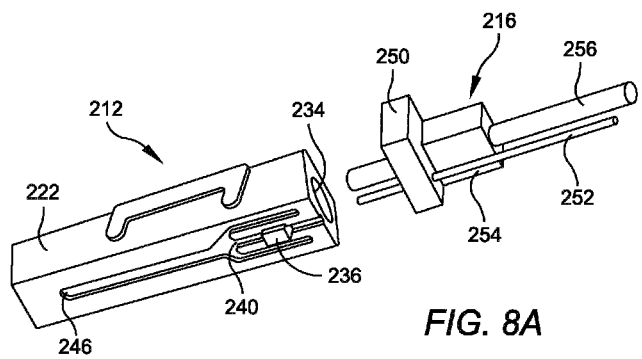
FIG. 8A is a perspective view of the cassette and a motor/drive system of the autoinjector system of FIG. 6 in position at the beginning and at the end of a duty cycle.

Referring collectively to FIGS. 8A-SC, one exemplary method of operation of the system 200 will now be described. Although the autoinjector 214 is not shown in FIGS. 8A-8C, the cassette 212 and the motor/drive system 216, shown therein, are to be considered as being operationally positioned within the autoinjector 214 as shown in FIG. 6. The motor/drive system 216 shown in FIG. 8A, includes a first (injection) motor 250 and section (delivery) motor 254. The motors 250 and 254 may comprise any suitable, well known type of motor including without limitation, stepper motors and reluctance motors. The motors 250 and 254 each includes a drive system for converting the rotary motion of the motor to linear motion. Such drive systems include without limitation, lead screw/worm gear drive systems, rack and pinion drive systems, and any other linear drive or transmission system. The drive system associated with the first motor 250 includes a drive rod 252 which is moved by the first motor 250. The drive system associated with the second motor 254 includes a pusher 256 which is moved by the second motor 254. The operations of the first motor 250 and the second motor 254 are both controlled by the microcomputer 218.

In overview, a duty cycle for the system 200 may be envisioned as a series of sequential changes in the configuration of cassette 212. For system 200, these configuration changes are caused by separate operations of the first motor 250 and the second motor 254. In compliance with these operations, a complete duty cycle for the system 200 will constitute, in order, configurations shown from FIG. 8A, to FIG. 8B, to FIG. 8C, and then in reverse order from FIG. 8C, back to FIG. 8B and FIG. 8A.

Figure 8B:
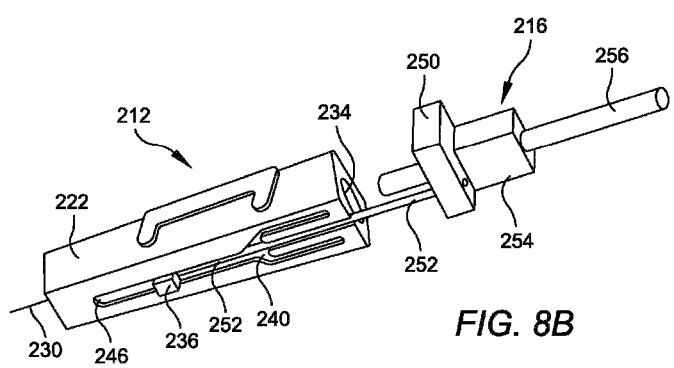
FIG. 8B is a view of the components shown in FIG. 8A with the syringe in the cassette being advanced by a first motor of the motor/drive system for insertion of the syringe needle into a patient.

FIG. 8A, shows the cassette 212 with the syringe 226 in a home position, which places the injection needle 230 in the needle concealed (proximal) position. In the home position, the protrusion 236 on inner sleeve 224 is held by the latch mechanism 240 on housing 222. Consequently, the injection needle 230 of the syringe 226 is held and concealed within the cassette 212. FIG. 8B shows the cassette 212 with the syringe 226 moved into an injection position via the first motor 250, which advances the drive rod 252, wherein the injection needle 230 has been extended from the cassette 12 through a hole 258 at the distal end 260 of the autoinjector 214 (FIG. 6). With this advancement, the drive rod 252 interacts with the latch mechanism 240 to release protrusion 236, thereby allowing a distal movement of the now unlatched syringe 226 and inner sleeve 224 on the housing 222. This movement is controlled by the microcomputer 218 and is performed with sufficient force to allow the injection needle 230 to penetrate into the skin tissue of a user/patient. Preferably, this movement of the syringe 226 from the home position (FIG. 8A) to the injection position (FIG. 8B) is accomplished at a speed of about 0.1 m/s to about 1.0 m/s. Further, the first motor 250 may be pre-programmed to stabilize the syringe 226 in the injection position.

With the syringe 226 in the injection position (FIG. 8B), the microcomputer 218 then activates the second motor 254 to move the pusher 256 against the plunger 232 in the fluid chamber 228 (FIG. 7). The microcomputer 218 may be pre-programmed to advance the plunger 232 at an appropriate speed for injection of the medicament, which typically comprises a fluid medicament, from the fluid chamber 228.

Figure 8C:
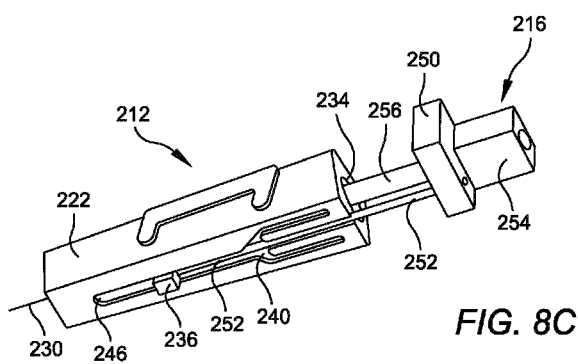
FIG. 8C is a view of the components shown in FIG. 8B with the plunger in the syringe being advanced by a second motor of the motor/drive system for injection of a fluid medicament from the syringe into the patient.

FIG. 8C shows the autoinjector assembly 200 after completion of the injection. As mentioned above, completion of the injection duty cycle requires the pusher 256 to be withdrawn. This withdrawal of the pusher 256 is accomplished by the second motor 254. Once the pusher 256 has been withdrawn (FIG. 8B), the first motor 250 is again activated by the microcomputer 218 to withdraw the drive rod 252. The drive rod 252 then pulls the protrusion 236 back and into engagement with the latch mechanism 240, thereby placing the syringe 226 in the home position and the injection needle 230 in the needle concealed (proximal) position. The cassette 212 can then be removed from the autoinjector 214 and discarded.

As an additional feature of the system 200, a sensor 262 may be provided at the distal end of the autoinjector 214. In one exemplary embodiment, the sensor 262 is positioned adjacent the hole 258 of the cassette 212. The sensor 262, in one exemplary embodiment, is of a type that will react to capacitance that can be measured between the sensor 262 and the skin of the user/patient. The sensor 262 determines when the autoinjector 214 is in physical contact with a user/patient's skin. The microcomputer 218 will operate a duty cycle for the system 200 only when such contact is indicated. Otherwise, there can be no operation of the system 200.

Figure 9:
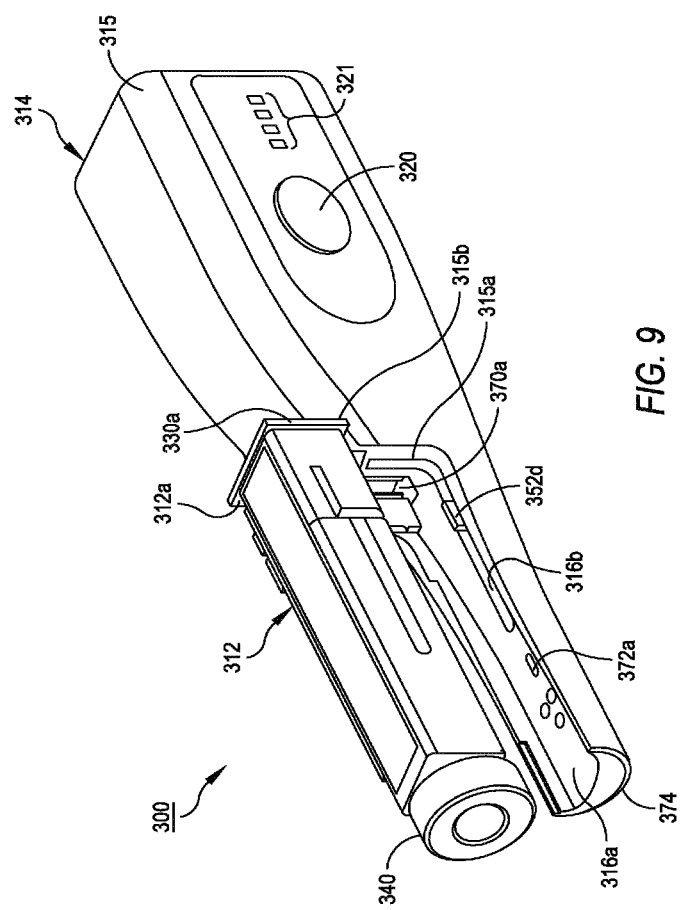
FIG. 9 is a perspective exploded view of yet another exemplary embodiment of the autoinjector system comprising reusable autoinjector and a corresponding disposable cassette.

FIG. 9 shows yet another exemplary embodiment of the autoinjector system generally designated by reference numeral 300. The system 300 generally includes a disposable cassette 312 and a re-useable autoinjector 314. The autoinjector 314 includes a housing 315 having a cut-out 315a for receiving the cassette 312. The autoinjector housing 315 further includes a recess 315b for receiving a pair of opposing, lateral tabs 312a formed on a proximal end of the cassette 312, when the cassette 312 is positioned in the cut-out 315a of the autoinjector housing 315. The recess 315b of the autoinjector housing 315 and the lateral tabs 330a of the cassette 312 cooperate to securely retain the cassette 312 on the autoinjector 314 and to prevent longitudinal movement of the cassette 312 when the autoinjector 314 is operated. The autoinjector housing 315 also includes an injection button 320 for activating the system 300 and a plurality of indicator lights 321 (e.g., LEDs) for indicating the status of the system 300. A skin sensing sensor 374 is provided at a distal end of the autoinjector 314 for sensing when the distal end of the autoinjector 314 is in physical contact with a user/patient's skin. The autoinjector system 300 will operate only when such contact is indicated. The cassette 312 includes a cap 340 inserted through an aperture (not visible) in a distal end of the cassette 312, which is used for gripping a protective needle shield that covers an injection needle of a syringe contained within the cassette 312, as will be explained in greater detail further on.

Figure 10A:
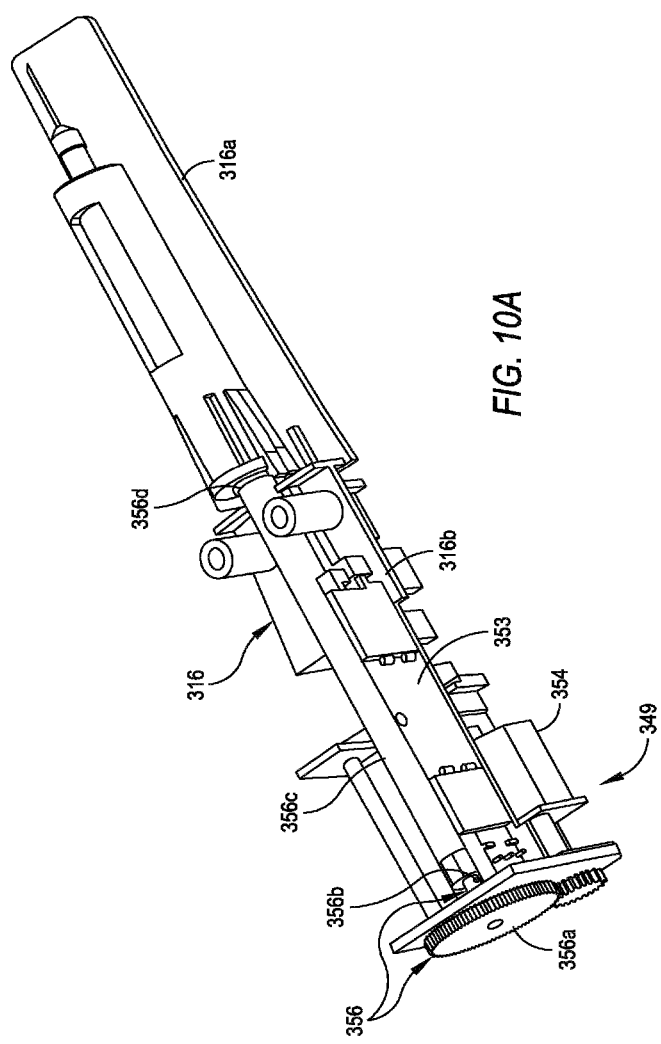
FIG. 10A is a perspective top view of an exemplary embodiment of an internal frame of an autoinjector similar to the one shown in FIG. 9 with a delivery motor/drive system attached thereto.
Figure 10B:
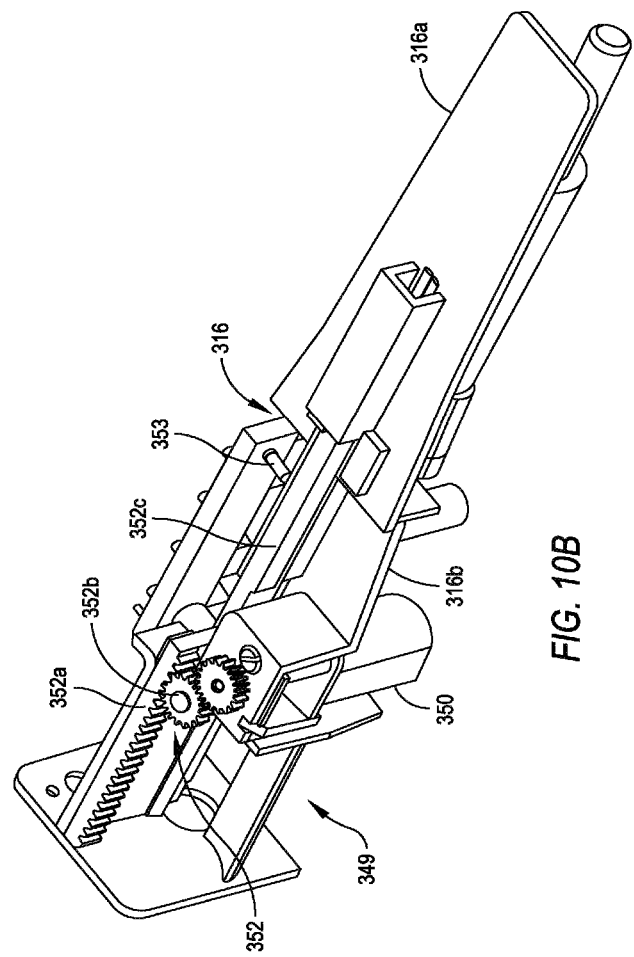
FIG. 10B is a perspective bottom view of the internal frame shown in FIG. 10A with a injection motor/drive system attached thereto.

Referring now to FIGS. 10A-10D and initially to FIG. 10A, the autoinjector 314 includes an elongated internal frame 316, which is rigidly secured within the autoinjector housing 315 (FIG. 9). The frame 316 includes a cassette support section 316a and motor/drive system and controller (MDC) support section 316b. The cassette support section 316a forms the bottom of the housing cut-out 315a and defines a mounting surface for the cassette 312 (FIG. 9). A motor/drive system 349 is rigidly mounted to MDC support section 316b of the internal frame 316. The motor/drive system 349 includes a first (injection) motor 350 (FIG. 10B) and a second (delivery) motor 354 (FIG. 10A). The first and second motors 350, 354 may comprise any suitable well-known type of motor including, without limitation, stepper motors and reluctance motors. Each of the first and second motors 350, 354 is associated with a drive system for converting the rotary motion of the motor to linear motion. Such drive systems include, without limitation, lead screw/worm gear drive systems, rack and pinion drive systems, and any other linear drive or transmission system that is capable of converting rotary motor motion into linear motion. As shown in FIG. 10B, the first motor 350 is associated with a rack and pinion drive system 352 including a rack member 352a and a pinion 353b, and as shown in FIG. 10A, the drive system associated with the second motor 354 comprises a lead screw drive system 356 comprising a gear drive 356a and lead screw 356b.

Referring again to FIG. 10B, the distal end of the rack member 352b of the rack and pinion drive system 352 forms a drive link 352c. As shown in FIG. 9, the drive link 352c has a free end 352d that extends up through a longitudinally extending, elongated opening 316b in the cassette support section 316a to operate a syringe insertion mechanism of the cassette 312. When the first motor 350 is operated, the rack and pinion drive system 352 moves the drive link 352c in a linear manner such that the free end 352d thereof moves distally and proximally in the longitudinal opening 316b of the cassette support section 316a. A first position sensor 353 is provided for sensing the position and speed of the drive link 352c, as will be explained further on.

Referring again to FIG. 10A, the lead screw 356b of the lead screw drive system 356 drives an elongated pusher 356c. The elongated pusher 356c has a free end 356d which operates a medicament delivery mechanism of the cassette 312. When the second motor 354 is operated, the lead screw drive system 356 moves the pusher 356a in a linear manner such that free end 356d thereof moves longitudinally within the autoinjector 314 in a distal or a proximal direction. A second position sensor 355 is provided for sensing the position and speed of the pusher 356a, as will be explained further on.

Figure 10C:
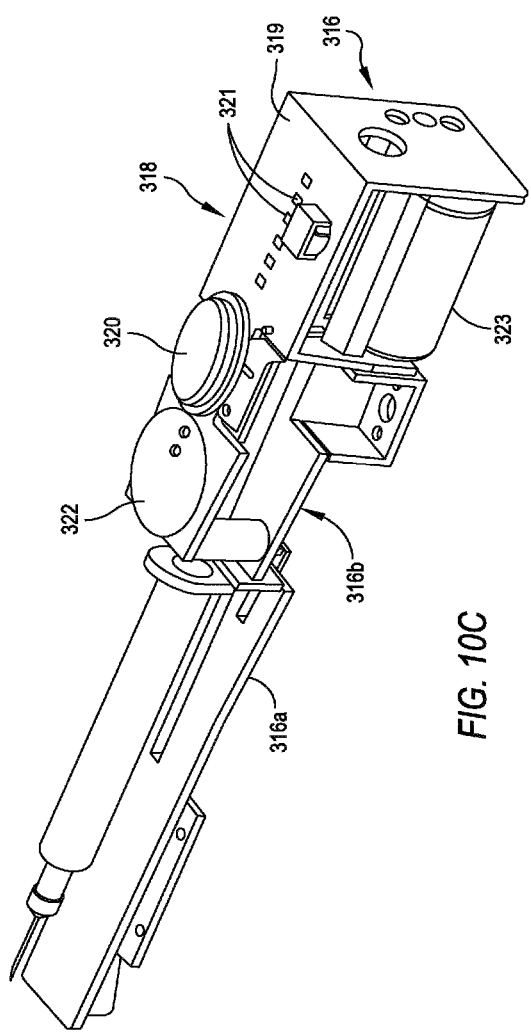
FIG. 10C is a perspective top view of the internal frame shown in FIG. 10A with autoinjector control components attached thereto.

Referring now to FIG. 10C, the MDC support section 316b of the internal frame 316 also supports certain control components of the autoinjector 314. These control components include a printed circuit board assembly 318 which defines a microcomputer or controller 319. The printed circuit board assembly 318 includes the injection button 320 and the indicator lights 321 described earlier, and an audible indicator in the form of a piezo-buzzer 322. The controller 319 executes one or more pre-determined programs that control the operation of the first and second motors 350 and 354. A power supply 323 for powering the first and second motors 350 and 354, and all the control components of the autoinjector 314, is also supported by the MDC support section 316b of the internal frame 316. In one exemplary embodiment, the power supply 323 comprises, without limitation, a control circuit, such as a step-up DC to DC convertor, and a battery, such as a rechargeable lithium battery.

As shown in FIG. 10D, the cassette support section 316a of the internal frame also supports certain control components of the autoinjector 314. These control components include a cassette detection switch 370, a speed selection switch 372, and the earlier described skin sensor 374. The power supply 323 also supports the power requirements of these control components. A flexible interconnect 371 is provided for connecting the cassette detection switch 370, the speed selection switch 372, and the skin sensor 374 with the printed circuit board assembly 318.

As shown in FIG. 9, the cassette detection switch 370 is actuated, in one exemplary embodiment, by an actuator button 370a that extends through an aperture in the cassette support section 316a and engages the cassette 312 when same is mounted on the cassette support section 316a. The speed selection switch 372 may be actuated by a button or like actuator 372a extending through another aperture in the cassette support section 316a. A distal end 374a of the skin sensor 374 forms a distal end of the autoinjector housing 315 so that it can make contact with a user/patient's skin.

Referring collectively to FIGS. 11A-11C, the cassette 312 includes a housing 330, an inner sleeve 331 slidably moveable in the housing 330, a hypodermic syringe 326 fixedly disposed in the inner sleeve 331, and the earlier described cap 340. The syringe 326 includes a fluid chamber 326a pre-filled with a predetermined dose of a fluid medicament of a predetermined viscosity, an injection needle 326b (shown with broken lines) extending from a distal end of the fluid chamber 326a, a removable needle shield 326c covering the injection needle 326b, and a plunger 326d moveable within the fluid chamber 326a for expelling medicament from the chamber 326a through the injection needle 326b. The viscosity of the fluid medicament typically ranges between about 1 centipoise to about 320 centipoise, although syringes with fluid medicaments having viscosities greater than 320 centipoise may also be used by appropriate selection of the second motor 354 and/or drive system 356.

Figure 12:
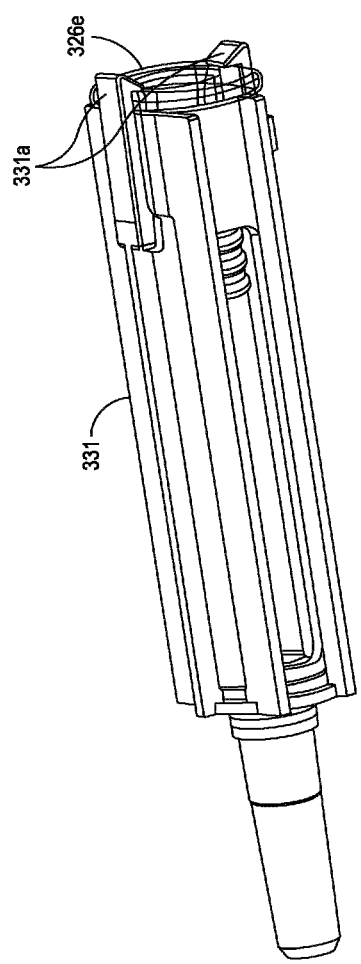
FIG. 12 is a perspective view of the an inner sleeve and syringe of a cassette similar to the one shown in FIGS. 9 and 11A-11C.

As shown in FIG. 12, the inner sleeve 331 includes a pair of locking detents 331a formed on a proximal end of the inner sleeve 331. The locking detents 331a are configured for engaging a finger flange 326e formed on the proximal end of the fluid chamber 326a of the syringe 326, to fixedly retain the syringe 326 in the inner sleeve 331.

Figure 13:
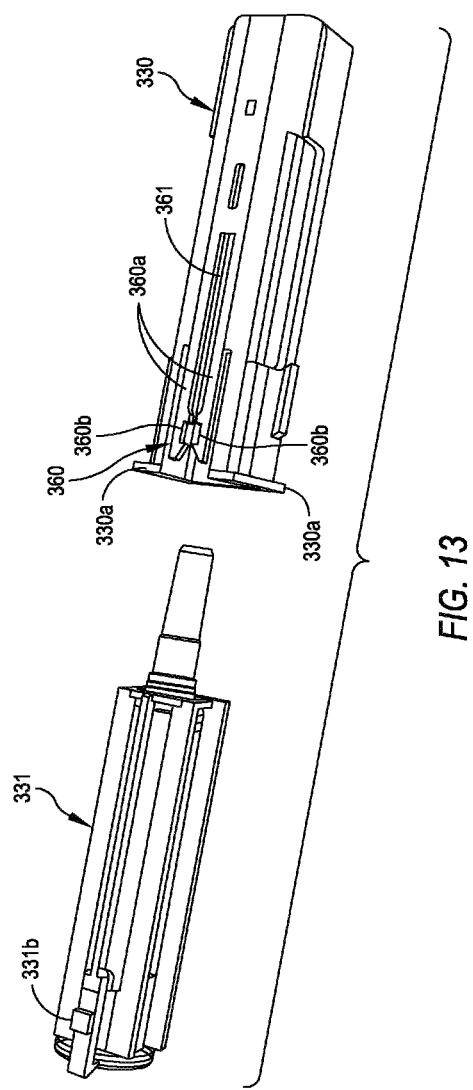
FIG. 13 is a perspective exploded view of the inner sleeve/syringe shown in FIG. 12 and a housing of the cassette similar to the one shown in FIGS. 9 and 11A-11C.
Figure 14:
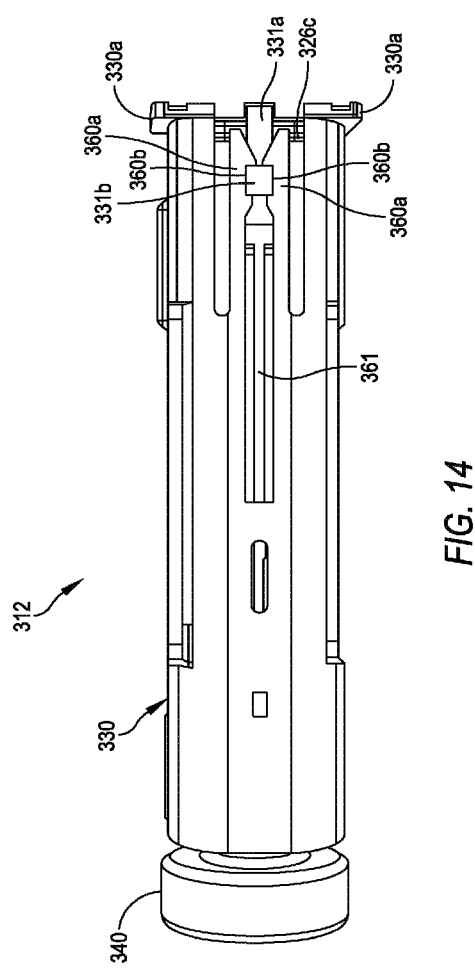
FIG. 14 is a bottom view of the cassette shown in FIG. 9.

As collectively shown in FIGS. 13 and 14, one of the locking detents 331a of the inner sleeve 331 includes a projection or protrusion 331b which engages a latch mechanism 360 formed on the cassette housing 330. The latch mechanism 360 includes a pair of opposed, resilient locking arms 360a that extend proximally from the proximal end of a longitudinally elongated slot 361 formed in a side of the housing 330. The locking arms 360a define locking detent slots 360b through which the protrusion 331b extends.

The cassette 312 is assembled, in one exemplary embodiment, by first inserting the pre-filled syringe 326 into the inner sleeve 331 so that the finger flanges 326e of the fluid chamber 326a are lockingly engaged by the locking detents 331a. The inner sleeve 331 with the pre-filled syringe 326, is then inserted into the housing 330 of the cassette 312 so that the protrusion 331b of the inner sleeve 331 spreads apart- and slides between the locking arms 360a of the housing 330 and then enters the detents slots 360b of the locking arms 360a, where it is latched. Once assembled, the syringe 326 is now in a home position with the injection needle 336b of the syringe 326 concealed in the housing 330 of the cassette 312 in a needle concealed (proximal) position. In an alternate embodiment, the cassette 312 is assembled by first inserting an empty inner sleeve 331 into the housing 330 of the cassette 312 and then inserting the pre-filled syringe 326 into the empty inner sleeve 331.

The first position sensor 353 is provided for sensing the position and speed of the drive link 352c. The position information provided by the first position sensor 353 may be used, in one exemplary embodiment, for identifying when the syringe 326 is in the home position and for determining when the syringe 326 is in a brake position, i.e., a position within the cassette just prior to the needled extended (distal) position. The syringe typically enters the brake position just after the injection needle 326b has penetrated the user/patient's skin. The brake position information allows the controller 319 to stop the first motor 350 quickly and in a manner that minimizes shock and vibration, when the inner sleeve 331/syringe 326 hit an end stop which defines the injection position. The speed information provided by the first position sensor 353 may be used for maintaining the speed of the syringe moving from the home position to the injection position.

The speed selection switch 372 has two or more settings, each of which corresponds to a different, user/patient selectable medicament injection speed (measured in seconds). This allows selection of a medicament injection speed that is most comfortable for the user/patient. In one exemplary embodiment, when the user/patient selects one of the two or more medicament injection speeds using the actuator 372a of the speed selection switch 372, the user/patient is actually setting the voltage applied to the second motor 354 to one of two or more different voltages. The actual medicament injection speed or speed of delivery, however, depends on the load force experienced by the second motor 354 (i.e., the load force applied to the plunger 326d by the pusher 356c). The load force, in turn, depends on the gauge and/or length of the injection needle, medicament viscosity, plunger/fluid chamber friction, motor and drive system tolerances, and cassette tolerances, and other system factors. When the load force experienced by the second motor 354 increases, the speed of the second motor 354 will decrease at the fixed voltage setting thereby decreasing the delivery time/rate of the autoinjector system 300. Similarly, when the load force experienced by the second motor 354 decreases, the speed of the second motor 354 will increase at the fixed voltage setting, thereby increasing the delivery time/rate of the autoinjector system 300. Therefore, in one exemplary embodiment, the controller 319 of the autoinjector 314 is pre-programmed with a feedback control program that compensates for the load force variations experienced by the second motor 354, thereby maintaining the medicament injection speed of the second motor 354. Accordingly, the autoinjector system 300 is capable of providing consistent delivery times/rates for each speed setting of the second motor 354. In one exemplary embodiment, the feedback control program executed by the controller 319 maintains the speed setting of the second motor 354 by measuring the speed of the pusher 356a, via the position sensor 355 and then, increasing or decreasing the voltage of the second motor 354 in real-time to maintain a constant pusher speed and therefore provide a constant delivery time/rate for the selected speed setting.

The following discussion describes one exemplary method for operating the autoinjector system 300. First, the user/patient sets the actuator of 372a the speed switch 372 to desired speed setting. The speed switch 372 allows the user/patient to set the second motor 354 to one of a plurality of different medicament injection rates (in seconds) of the autoinjector system 300. FIG. 15 is a table showing injection rates (in seconds) of three different samples (CM2-1, CM2-2, CM2-3) of the autoinjector system 300 set at low, medium, and high delivery motor speed settings for solutions of three different viscosities in centipoise (cP) (1 cP, 19 cP and 29 cP). In one exemplary embodiment, the second motor 354 and drive system 356 are selected to exert up to about 34 pounds of force on the plunger 326d of the syringe 326 (which equates to about 700 psi inside of the fluid chamber 326a of the syringe 326). In other embodiments, the second motor 354 and drive system 356 may be selected to exert more than 34 pounds of force on the plunger 326d of the syringe 326.

Next, the cassette 312 is mounted onto the autoinjector 314 by placing the cassette 312 into the cut-out of the autoinjector housing 315 so that the cassette 312 rests on the cassette support member 316a with the lateral tabs 330a of the cassette housing 330 disposed in the recess 315b of the autoinjector housing 315, (FIG. 9). When so mounted, the cassette 312 depresses the actuator 372a of the cassette detection switch 372 and the protrusion 331b of the cassette inner sleeve 331 engages the free end 352d of the drive link 352c. With the cassette detection switch actuator 372a depressed, the controller 319 will cause audible indicator 322 to sound and the indicator lights 312 to blink in a manner which indicates that the system is ready for use. The user/patient then removes the cap 340 from the cassette 312, thereby removing the needle shield from the syringe 326 and withdrawing it from inside the cassette 312. Next, the user/patient places the distal end of the autoinjector 315 against the user/patient's skin. If the skin sensor senses the user/patient's skin, the controller 319 will cause the indicator lights to light steadily, indicating to the user/patient that the autoinjector system 300 is ready to inject. The user/patient starts the injection by pressing the injection button 320 which energizes the first motor 350 in a first rotary direction, which advances the drive link 352c in the distal direction thereby unlatching the protrusion 331b of the inner sleeve 331 from the latch mechanism 360, thereby allowing a distal movement of the now unlatched inner sleeve 331 containing the syringe 326, relative to the cassette housing 330. The drive link 352c, therefore, moves the syringe 326 from the home position, where the needle 326b is in the needle concealed (proximal) position to the injection position, where the needle 326b is in a needle extended (distal) position and penetrating into the skin tissue of the user/patient. The first motor 350 and drive system 352 are both selected to provide a syringe injection speed, (the speed of the syringe moving from the home position to the injection position) of about 0.01 m/s to about 5.0 m/s, although other syringe injection speeds are possible by selection of an appropriate motor and/or drive system. In other embodiments, the syringe injection speed ranges between about 0.1 m/s to about 1.0 m/s. In some embodiments, a second speed position switch (not shown) may be provided for allowing the user/patient to select between two or more syringe injection speeds, to make the needle injection more comfortable.

With the syringe 326 now in the injection position, the controller 319 energizes the second motor 354 in a first rotary direction, which advances the pusher 356c in the distal direction against the plunger 326d in the fluid chamber 326a of the syringe 326 to inject the fluid medicament from the fluid chamber 326a of the syringe 326. In one embodiment, the controller 310 pauses the autoinjector 314 after completion of the fluid medicament injection to allow pressure to dissipate in the syringe 326 so that all the medicament is delivered and no "dribbling" of medicament occurs. Upon completion of the fluid medicament injection, the controller 319 energizes the second motor 354 in a second rotary direction, which pulls the pusher 356c in the proximal direction, thereby partially withdrawing the pusher 356c from the fluid chamber 326a of the syringe 326 to allow the injection needle to be withdrawn from the user/patient. Once the pusher 356 has been partially withdrawn, the controller 319 energizes the first motor 350 in a second rotary direction, which pulls the drive link 352c back in the proximal direction. Because the free end of the drive link 352c is coupled to the protrusion 331b of the inner sleeve 331, the drive link 352c pulls the inner sleeve 331 containing the spent syringe 326 back to the home position where the protrusion 331b is again latched by the latch mechanism 340, thereby placing the injection needle 330 in the needle concealed (proximal) position again. The controller 319 then energizes the second motor 354 again in the second rotary direction to fully withdraw the pusher 356c from the fluid chamber 326a of the syringe 326. The cassette 312 can now be removed from the autoinjector 314 and discarded.

The autoinjector system 300 may be suitably adapted to provide any desired medicament injection rate. In one exemplary embodiment of the autoinjector system, the medicament injection rates range between about 2.0 seconds and about 15.0 seconds.

In one exemplary embodiment of the autoinjector system, the medicament comprises a fluid medicament having a viscosity of about 1 centipoise and the medicament injection rates range between about 2.9 seconds and about 5.0 seconds.

In another exemplary embodiment of the autoinjector system, the medicament comprises a fluid medicament having a viscosity of about 19 centipoise and the medicament injection rates range between about 4.4 seconds and about 9.6 seconds.

In a further exemplary embodiment of the autoinjector system, the medicament comprises a fluid medicament having a viscosity of about 29 centipoise and the medicament injection rates range between about 7.5 seconds and about 11.8 seconds.

In one exemplary embodiment of the autoinjector system, the medicament comprises a fluid medicament having a viscosity of about 19 centipoise.

In another exemplary embodiment of the autoinjector system, the medicament comprises a fluid medicament having a viscosity ranging between about 1 centipoise and about 320 centipoise.

In still another exemplary embodiment of the autoinjector system, the medicament comprises a fluid medicament having a viscosity ranging between about 5 centipoise and about 40 centipoise.

In yet another exemplary embodiment of the autoinjector system, the medicament comprises a fluid medicament having a viscosity ranging between about 10 centipoise and about 35 centipoise.

In a further exemplary embodiment of the autoinjector system, the medicament comprises a fluid medicament having a viscosity ranging between about 15 centipoise and about 30 centipoise.

In still a further exemplary embodiment of the autoinjector system, the medicament comprises a fluid medicament having a viscosity ranging between about 20 centipoise and about 25 centipoise.

In still a further exemplary embodiment of the autoinjector system, the medicament comprises a fluid medicament having a viscosity ranging between about 16 centipoise and about 42 centipoise.

In yet a further exemplary embodiment of the autoinjector system, the medicament comprises a fluid medicament having a viscosity ranging between about 1 centipoise and about 29 centipoise.

Figure 16:
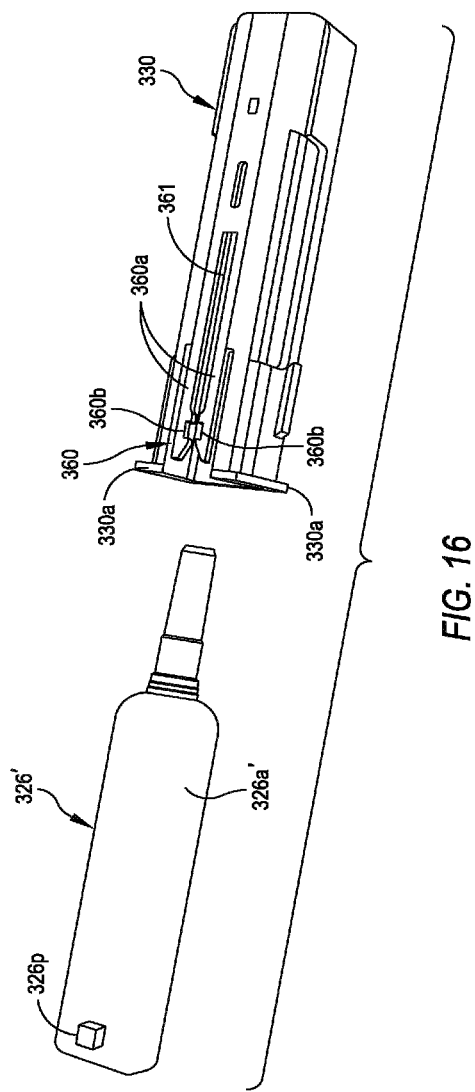
FIG. 16 is a perspective exploded view of an alternate embodiment of the cassette that omits the inner sleeve.

FIG. 16 shows an alternate embodiment of the cassette designated by reference numeral 326'. The inner sleeve shown in the embodiment of FIGS. 11A-11C and 12-14 has been omitted and the fluid chamber 326a' of the syringe 326' has been provided with a projection or protrusion 326p that engages the latch mechanism 360 formed on the cassette housing 330. The free end 352d of the drive link 352c of the autoinjector 314 (FIG. 9) engages the protrusion 326p to move the syringe 326' from the home position to the injection position.

Although the autoinjector system and its elements have been described in terms of exemplary embodiments, it is not limited thereto. Rather, the appended claims should be construed broadly, to include other variants and embodiments of the autoinjector system and its elements, which may be made by those skilled in the art without departing from the scope and range of equivalents of the system and its elements.

What is claimed is:

1. A system for injecting a medicament into a patient, the system comprising:
    an injector; and
    a medicament cassette;
    the medicament cassette comprising:
        a housing comprising one or more walls having a lateral opening extending therethrough in a direction perpendicular to a longitudinal axis of the housing;
        a sleeve movable in the housing between first and second positions; and
        a syringe comprising a chamber for containing a medicament and an injection needle extending from the chamber, the syringe fixed with the sleeve to move along therewith, with the chamber at least partially disposed in the sleeve, the injection needle having a skin penetrating end opposite the syringe chamber, the skin penetrating end of the injection needle being disposed within the housing when the sleeve is in the first position and the skin penetrating end of the injection needle extending out from the housing when the sleeve is in the second position;
    the injector comprising:
        a surface for removably mounting the cassette thereon;
        a motor driven link having a first end engageable with a portion of the sleeve when the cassette is mounted on the surface, wherein the portion of the sleeve extends laterally outwardly therefrom and at last partially through the opening of the housing, the link configured to engage the portion of the sleeve to move the sleeve from the first position to the second position.

2. The system according to claim 1, wherein the injector further comprises a motor driven plunge rod for expelling the medicament contained in the chamber of the syringe through the injection needle and out the skin penetrating end thereof at a specified delivery rate.

3. The system according to claim 2, further comprising a motor for driving the plunge rod, the motor being speed adjustable to allow a user to select the delivery rate of the medicament expelled out through the skin penetrating end of the injection needle.

4. The system according to claim 3, further comprising a controller for automatically maintaining the selected delivery rate of medicament.

5. The system of claim 1, wherein the portion of the sleeve comprises a projection extending from a surface of the sleeve.

6. The system of claim 5, wherein the housing includes a latch that releasably engages the projection when the sleeve is in the first position.

7. The system of claim 6, wherein the latch includes at least one resilient arm with a detent slot.

8. The system of claim 1, wherein the housing includes a latch that releasably engages the portion of the sleeve, when the sleeve is in the first position.

9. The system of claim 8, wherein the latch includes at least one resilient arm with a detent slot.

10. The system of claim 1, wherein the sleeve includes a locking detent for fixedly retaining the syringe in the sleeve.

11. The system of claim 10, wherein the portion of the syringe comprises a projection extending from a surface of the locking detent.

12. The system of claim 1, wherein the surface of the injector defining an elongated opening; and the first end of the link extends through the elongated opening to engage the portion of the sleeve when the cassette is mounted on the surface.

13. A system for injecting a medicament into a patient, the system comprising:
    an injector; and
    a medicament cassette; the medicament cassette comprising:
        a housing comprising one or more walls having a lateral opening extending therethrough in a direction perpendicular to a longitudinal axis of the housing; and
        a syringe comprising a chamber for containing a medicament and an injection needle extending from the chamber, the injection needle having a skin penetrating end opposite the chamber, the syringe movable with respect to the housing from a first position with the chamber and the skin penetrating end disposed within the housing and a second position with the chamber disposed within the housing and the skin penetrating end extending out from the housing;
    the injector comprising:
        a surface for removably mounting the cassette thereon;
        a motor driven link having a first end engageable with a portion of the syringe when the cassette is mounted on the surface, wherein the portion of the syringe extends laterally outwardly therefrom and at least partially though the opening of the housing, the link configured to engage the portion of the syringe to move the syringe from the first position to the second position.

14. The system of claim 13, wherein the portion of the syringe comprises a projection extending from a surface of the chamber.

15. The system of claim 14, wherein the projection extends radially outwardly from the surface of the chamber.

16. The system of claim 14, wherein the surface of the injector defines an elongated opening; and the first end of the link extends through the elongated opening to engage the portion of the sleeve when the cassette is mounted on the surface.

17. A medicament cassette for an autoinjector, the medicament cassette comprising:
   a housing comprising one or more walls having as lateral opening extending therethrough in a direction perpendicular to a longitudinal axis of the housing; and
   a syringe comprising a chamber for containing a medicament and an injection needle extending from the chamber, the injection needle having a skin penetrating end opposite the chamber, the syringe movable with respect to the housing from a first position with the chamber and the skin penetrating end disposed within the housing and a second position with the chamber disposed within the housing and the skin penetrating end extending out from the housing, wherein the syringe comprises a portion extending laterally outwardly therefrom at last partially through the opening of the housing, the portion of the syringe configured to be engaged by a drive link of the autoinjector to drive the syringe from the first position to the second position when the cassette is mounted on or in the autoinjector.

18. The cassette of claim 17, wherein the portion of the syringe comprises a projection extending from a surface of the syringe chamber.

* * * * *